United States Patent
Jönsson et al.

(10) Patent No.: US 8,293,113 B2
(45) Date of Patent: Oct. 23, 2012

(54) HEAT EXCHANGER AND METHOD FOR HEAT EXCHANGING

(75) Inventors: Lennart Jönsson, Bjärred (SE); Jan Sternby, Lund (SE); Eddie Nilsson, Höör (SE)

(73) Assignee: Gambro Lundia AB, Lund (SE)

( * ) Notice: Subject to any disclaimer, the term of this patent is extended or adjusted under 35 U.S.C. 154(b) by 0 days.

(21) Appl. No.: 13/123,071

(22) PCT Filed: Oct. 9, 2009

(86) PCT No.: PCT/EP2009/063159
§ 371 (c)(1),
(2), (4) Date: Apr. 7, 2011

(87) PCT Pub. No.: WO2010/040824
PCT Pub. Date: Apr. 15, 2010

(65) Prior Publication Data
US 2011/0198289 A1    Aug. 18, 2011

Related U.S. Application Data

(60) Provisional application No. 61/104,275, filed on Oct. 10, 2008.

(30) Foreign Application Priority Data

Oct. 10, 2008 (SE) .................................. 0802131

(51) Int. Cl.
*B01D 61/30* (2006.01)
*B01D 61/24* (2006.01)
*B01D 61/28* (2006.01)
*B01D 69/06* (2006.01)
*A61M 1/34* (2006.01)

(52) U.S. Cl. ........ 210/650; 210/175; 210/181; 210/252; 210/258; 210/645; 210/646

(58) Field of Classification Search .................. 210/645, 210/646, 650, 175, 181, 252, 258
See application file for complete search history.

(56) References Cited

U.S. PATENT DOCUMENTS
4,272,373 A     6/1981    Stenberg et al.
(Continued)

FOREIGN PATENT DOCUMENTS
DE           101 37 888 A1      5/2002
(Continued)

OTHER PUBLICATIONS

European Search Report for PCT/EP2009/063159 mailed Feb. 12, 2010. European Search Report for PCT/EP2009/063148 mailed Feb. 10, 2010.

*Primary Examiner* — John Kim
(74) *Attorney, Agent, or Firm* — Nixon & Vanderhye P.C.

(57) ABSTRACT

A method for exchanging heat between an effluent fluid and a treatment fluid and a heat exchanger for heat exchange as well as an arrangement and a kit comprising a heat exchanger. The heat exchanger comprises a first and a second fluid circuit extending through the heat exchanger. The heat exchanger further comprises a stack of fluid plates and a membrane arranged between each of the fluid plates where one interspace is formed between each fluid plate and membrane. The first and the second fluid circuit is each constituted by a passage extending through the fluid plates and membranes and along the fluid plates and membranes in at least two interspaces. According to the method for heat exchanging an effluent fluid is passed through the first fluid circuit and a treatment fluid is passed through the second fluid circuit such that the effluent fluid is passed along one side of a membrane and simultaneously the treatment fluid is passed along the other side of the membrane. Heat is thus exchanged between the effluent fluid and the treatment fluid over the membrane.

32 Claims, 20 Drawing Sheets

U.S. PATENT DOCUMENTS

| | | |
|---|---|---|
| 4,411,872 A | 10/1983 | Bramson |
| 5,829,517 A | 11/1998 | Schmid et al. |
| 6,349,170 B1 | 2/2002 | Fressinet et al. |
| 6,893,619 B1 | 5/2005 | James et al. |

FOREIGN PATENT DOCUMENTS

| | | |
|---|---|---|
| GB | 2 019 550 | 10/1979 |
| JP | 11-142982 | 5/1999 |
| JP | 2002-195777 | 7/2002 |
| JP | 2006-010130 | 1/2006 |

HEAT EXCHANGER AND METHOD FOR HEAT EXCHANGING

CROSS RELATED APPLICATIONS

This application is the US national phase of international application PCT/EP2009/063159 filed 9 Oct. 2009 and claims priority to Swedish Patent Application No. 0802131-3 filed 10 Oct. 2008 and U.S. Provisional Application No. 61/104,275 filed 10 Oct. 2008 which designated the U.S. and the entire contents of each of these applications are hereby incorporated by reference.

TECHNICAL FIELD OF THE PRESENT INVENTION

The present invention relates to an arrangement and a disposable kit including a heat exchanger and a method for exchanging heat between a primary fluid and at least a first secondary fluid.

BACKGROUND OF THE INVENTION

Treatment fluids required in treatment of a patient by continuous renal replacement therapy, hereinafter referred to as CRRT, must often be stored in a temperature which is relatively cold with respect to the patient's body temperature. Such fluids are typically stored at temperatures ranging from 2° to 20° Celsius in order to preserve the fluids in a state so that the function and integrity of the fluid is maintained. For this reason it is often desirable to heat the fluid to an appropriate temperature when introducing it into the patient's body to prevent any rapid decrease in the patient's body temperature. For the same reason it is desirable to heat fluids that are in contact with blood via a semi permeable membrane in a blood treatment unit or the blood as such before the blood is reintroduced to the patients body.

In dialysis treatment some heat is generally lost to the environment from the blood circulating in an extracorporeal circuit comprising a bloodline and a dialyzer in which the blood is treated. Heat loss from the blood in the extracorporeal circuit, in time, results in loss of heat from the patient's body.

The continuous nature of CRRT increases the potential of heat loss from the blood circulating in the extracorporeal circuit and the patient may, under certain circumstances, experience a depression of corporeal temperature. This is especially significant when the treatment fluid has a temperature lower than the extracorporeally circulated blood.

Loss of heat from the extracorporeally circulated blood is due to diffusion of heat either to the surrounding air or by diffusion or convection to the effluent fluid. Effluent fluid is constituted by the dialysis fluid used in the treatment in hemodialysis (HD) mode as well as the fluid extracted in hemodiafiltration (HDF) or hemofiltration (HF) mode. Effluent fluid is sent to a drain whereby the heat diffused from the blood to the effluent fluid is lost. Also the infusion of treatment fluid to the blood may result in decreased temperature of the blood.

Usually the main part of the heat in the blood is lost to the effluent fluid. A special challenge occurs during periods of low blood flow, about 50 ml/min, since the temperature decrease is larger compared with periods of medium blood flows, in the range of 100-200 ml/min, or high blood flows, in the range of 200-300 ml/min.

For this reason it is desirable in some CRRT treatments to compensate for, or to reduce, heat loss from the extracorporeally circulating blood.

In case the treatment fluids are stored sterile in flexible bags or rigid or semirigid containers it is a challenge to heat the treatment fluid by means of devices requiring direct contact with the fluid. To make sure that the extracorporeally circulated blood is not severely affected the temperature of any treatment fluid should not exceed 41° Celsius.

U.S. Pat. No. 6,349,170 discloses a renal replacement therapy system comprising a blood warmer capable of being attached to a renal replacement therapy monitor and a venous line adapted to be received by and cooperate with the blood warmer. The blood warmer comprises an external cylindrical surface. The venous line is engaged helically on the cylindrical surface serving as a heat exchanging section of the blood warmer. A clam-shell helical sleeve is installed over the heat exchange section to hold the venous line in place and to improve the heat transfer characteristics from the heat exchange section to the venous line.

SUMMARY OF THE INVENTION

It is an object of the present invention to provide a heat exchanger, an arrangement and a disposable kit comprising a heat exchanger, and a method for exchanging heat which incorporates means and steps for compensating for some of the heat lost from blood in an extracorporeal circuit.

One embodiment of the present invention makes use of the fact that heat loss from the blood may be accepted to a certain extent. For example a heat loss rate corresponding to an energy loss in the range of 40 W may be accepted for an adult patient.

The present invention is based on recovering the heat lost from the blood to the effluent fluid. Thus, treatment fluids to be infused to the blood or to dialyse the blood are heated by means of the effluent fluid that in its turn has been heated by the blood. The blood per se is not heated.

According to one embodiment of the invention the heat exchanger is of plate type. The heat exchanger comprises a first and a second fluid circuit. Optionally the heat exchanger comprises a third fluid circuit. In a further embodiment the heat exchanger comprises a fourth fluid circuit. The fluid circuits are separate from each other and each extends through the heat exchanger from one side to an opposite side. Further the heat exchanger comprises a stack of fluid plates and a membrane arranged between each of the fluid plates such that one interspace is formed between one side of a fluid plate and one side of a membrane. Each of the fluid circuits is constituted by a passage extending through the fluid plates and membranes and in at least two interspaces.

According to one embodiment of the invention the first fluid circuit is constituted by a passage extending in at least four interspaces.

According to one embodiment of the invention the first fluid circuit is constituted by a passage extending in at least eight interspaces, the second fluid circuit is constituted by a passage extending in at least four interspaces and the third fluid circuit is constituted by a passage extending in at least four interspaces.

In one embodiment of the heat exchanger a multiple of fluid plates with intermediate membranes are piled on top of each other and arranged between an upper and a lower end plate. The upper and lower end plates are a type of fluid plate adapted for passing fluid on one side only. The respective end plates are optionally integrated with each other to form a housing enclosing the pile of fluid plates and membranes.

According to one embodiment of a method for exchanging heat between a primary fluid and a secondary fluid in a heat exchanger of the above mentioned type the primary fluid is passed through a first fluid circuit and the secondary fluid is passed through a second fluid circuit. The method comprises the following steps; passing the primary fluid along one side of a membrane and simultaneously passing the secondary fluid along the other side of the membrane and exchanging heat between the primary fluid and the secondary fluid over the membrane.

According to one embodiment of a method for exchanging heat between a primary fluid and a first and a second secondary fluid in a heat exchanger of the disclosed type, the primary fluid is passed through a first fluid circuit and the first secondary fluid is passed through a second fluid circuit and the second secondary fluid is passed through a third fluid circuit. The method according to this embodiment comprises the following steps; passing the primary fluid along one side of a first membrane and simultaneously passing the first secondary fluid along the other side of the first membrane and subsequently passing the primary fluid along one side of a second membrane and simultaneously passing the second secondary fluid along the other side of the second membrane and exchanging heat between the primary fluid and the first secondary fluid over the first membrane and exchanging heat between the primary fluid and the second secondary fluid over the second membrane.

In one embodiment of the method for exchanging heat between a primary fluid and a first and a second secondary fluid according to the present invention the primary fluid flow is arranged to pass through the heat exchanger such that it alternatingly heats the first and the second secondary fluid. Optionally the primary fluid is arranged to heat also a third secondary fluid in a corresponding way. The primary fluid flow is optionally countercurrent to each of the secondary fluid flows or countercurrent to at least one of the secondary fluid flows.

The expression "alternatingly" as used herein is intended to include the concept of heating by means of a primary fluid, in a sequence, e.g. the first, the second, the first and the second secondary fluid etc as well as in a sequence heating e.g. the first, the second, the second and the first secondary fluid etc. I.e. the expression "alternatingly" as used herein is intended to include the concept of heating at least two secondary fluids by means of one primary fluid where the fluid circuits of the first and the secondary fluids are interlaced.

In one embodiment at least one of the fluid plates is provided with fluid channels on each of its sides for passing fluid. In one embodiment all of the fluid plates, but the upper and lower end plate, are provided with fluid channels on both sides.

In one embodiment at least one of the fluid circuits extends from one side, e.g. the upper side of the heat exchanger, and through all the plates and membranes to an opposite side of the heat exchanger, e.g. the lower side of the heat exchanger. In an alternative embodiment all the fluid circuits extends from one side to an opposite side of the heat exchanger thus maximizing the heat exchanging surface.

In one embodiment at least one of the fluid plates is thermally isolating, i.e. non conductive. Alternatively at least one of the fluid plates is thermally isolating only to such extent that the heat exchange over the fluid plate does not substantially influence the overall heat exchanging effect of the heat exchanger. In one embodiment all of the fluid plates are substantially thermally isolating or isolating.

By recovering the heat lost to the effluent fluid to heat the treatment fluids the method results in reducing the heat loss from the extracorporeally circulated blood in a continuous renal replacement therapy (CRRT).

According to one embodiment of the invention an arrangement for a continuous renal replacement therapy (CRRT) comprises a continuous renal replacement monitor with at least one blood pump, at least one treatment fluid pump and optionally an effluent pump. Such arrangement further comprises a disposable blood line associated with the monitor for extracorporeally circulating blood by means of the blood pump, a fluid distribution circuitry associated with the monitor comprising a line for passing effluent fluid, optionally by means of the effluent fluid pump, and at least one line for a treatment fluid associated with the monitor for passing treatment fluid by means of the treatment fluid pump. The treatment fluid is prepared in advance and ready to use. The arrangement also comprises a filtration unit arranged between the blood line and the fluid processing circuit. The fluid distribution circuitry further comprises a heat exchanger that is configured to be fluidly coupled to the effluent fluid line and disposed in thermal relationship with the treatment fluid line so as to provide for transfer of heat from the effluent fluid to the treatment fluid to be heated.

In the embodiment described above where the arrangement does not include any effluent pump, the pressure created by the blood pump is relied on for passing the effluent fluid. Optionally gravity facilitates passing of the effluent fluid.

According to one embodiment a disposable kit comprises a support element, a blood line, a fluid distribution circuitry comprising an effluent line and at least one treatment fluid line. All the lines are associated to the support element and at least each treatment fluid line having a U-shaped portion designed to cooperate with a respective pump. A filtration unit is associated with the blood line and with the fluid processing circuit. The fluid distributing circuitry comprises a heat exchanger that is configured to be fluidly coupled to the effluent fluid line and disposed in thermal relationship with the treatment fluid line so as to provide for transfer of heat from the effluent fluid to the fluid to be heated.

The heat exchanger according to the present invention performs throughout the whole range of flow rates viable for heat exchanging between a primary fluid, e.g. an effluent fluid, and at least one secondary fluid, e.g. a treatment fluid or blood fluid.

Further embodiments, features and advantages of the invention will become apparent from the following description, the drawings and the claims.

DETAILED DESCRIPTION OF THE INVENTION

Figure 1:
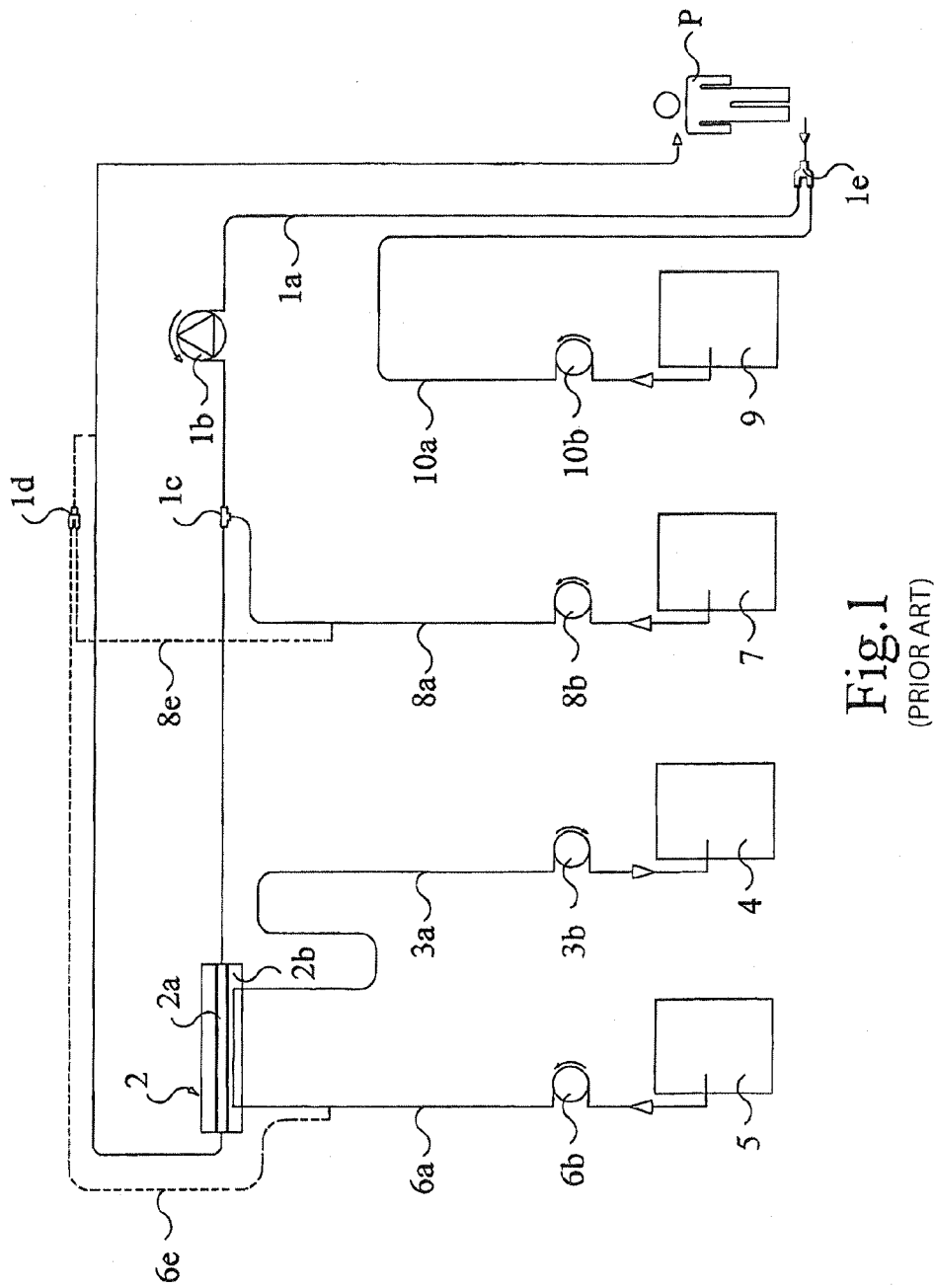
FIG. 1 schematically illustrates a CRRT flow diagram according to prior art.

FIG. 1 shows a schematic arrangement for continuous renal replacement therapy, CRRT. The arrangement comprises a blood circuit 1a for extracorporeally circulating blood from a patient P through a first compartment 2a of a filtration unit 2 by means of at least one blood pump 1b (by way of example only one blood pump is shown). The first compartment 2a of the filtration unit 2 is in FIG. 1 represented by a single semipermeable membrane of hollow fiber type. The arrangement further comprises an effluent line 3a for transferring effluent fluid from a second compartment 2b of the filtration unit 2 to an effluent fluid container 4 by means of an effluent fluid pump 3b. The arrangement comprises one or more treatment fluid lines such as lines for passing fresh dialysis fluid and/or replacement fluid and/or anticoagulation fluid. The CRRT therapy is monitored and controlled by means of a CRRT monitor (not shown). The monitor may be microprocessor-based. The monitor may contain all logic and receive and process commands by controlling valves (not shown) and pumps, interpret sensors (not shown), activate alarms and direct the operation of all aspects of the therapy system.

CRRT may be carried out in three different modes depending on the principle for solute removal: hemodialysis (HD) mode, hemofiltration (HF) mode and hemodiafiltration (HDF) mode.

In HD mode, where the solute removal in the filtration unit 2 is based on diffusion, fresh dialysis fluid is transferred from a dialysis fluid source 5 via a dialysis fluid line 6a by means of a dialysis fluid pump 6b to the second compartment 2b of the filtration unit 2. The dialyis fluid used in the filtration unit 2 is transferred to the effluent container 4 via the effluent line 3a by means of the effluent pump 3b.

In HF mode, where the solute removal in the filtration unit 2 is based on convection, the filtrate, i.e. the liquid that has been filtered from the patients blood, through the semipermiable membrane, is transferred from the second compartment 2b of the filtration unit 2 to the effluent container 4 via the effluent line 3a by means of the effluent pump 3b. In order to replace some of the filtrate and regain a normal body fluid status of the patient, a replacement fluid from a replacement fluid source 7 is infused into the blood line 1a at an infusion point 1c arranged upstream the filtration unit 2. The replacement fluid is transferred to the infusion point 1c in the blood line 1a via a replacement fluid line 8a by means of a replacement fluid pump 8b. Alterntively the replacement fluid from the replacement fluid source 7 is infused at an infusion point 1d downstream the filtration unit 2. The replacement fluid is then transferred to the infusion point 1d via the replacement fluid lines 8a, 8e by means of the replacement fluid pump 8b.

The volume of replacement fluid is controlled by means of the CRRT monitor such that it is less than the volume of filtrate. In an alternative CRRT configuration the replacement fluid is constituted by dialysis fluid in the dialysis fluid source 5 and transferred to the infusion point 1d in the blood line 1a via the dialysis fluid lines 6a, 6e by means of the dialysis fluid pump 6b.

In HDF mode, where the solute removal is based on diffusion and convection, both fresh dialysis fluid and replacement fluid is made use of according to the principles described above in connection with HD and HF mode.

In all three modes optionally an anticoagulant fluid from an anticoagulation fluid source 9 is infused into the blood line 1a at an infusion point 1e arranged upstream the bloodpump 1b. The anticoagulant fluid is passed to the infusion point 1e via an anticoagulation line 10a by means of an anticoagulation fluid pump 10b.

The respective sources for dialysis fluid 5, replacement fluid 7 and anticoagulant fluid 9 may all be in the form of containers with sterilized and ready for use fluids that are prepared in advance. Each container may contain a volume of fluid in the range of 1-10 litres. The container may be flexible, rigid or semirigid.

The dialysis fluid, the replacement fluid and the anticoagulant fluid may all be cold fluids relatively to the effluent fluid. Also the blood fluid may be colder than the effluent fluid. The present invention suggests to make use of the temperature difference between the effluent fluid and one or more of the following fluids: dialysis fluid, replacement fluid, anticoagulant fluid, blood fluid and blood plasma. The temperature difference is made use of such that the warmer effluent fluid is used to warm one or more of the colder fluids. The warming takes place in a heat exchanger arranged in thermal relationship with the effluent fluid so as to provide for transfer of heat from the effluent fluid to the colder fluid to be heated. The relatively warmer fluid and the relatively colder fluid will hereinafter be referred to as the primary fluid and the secondary fluid respectively.

Figure 2A:
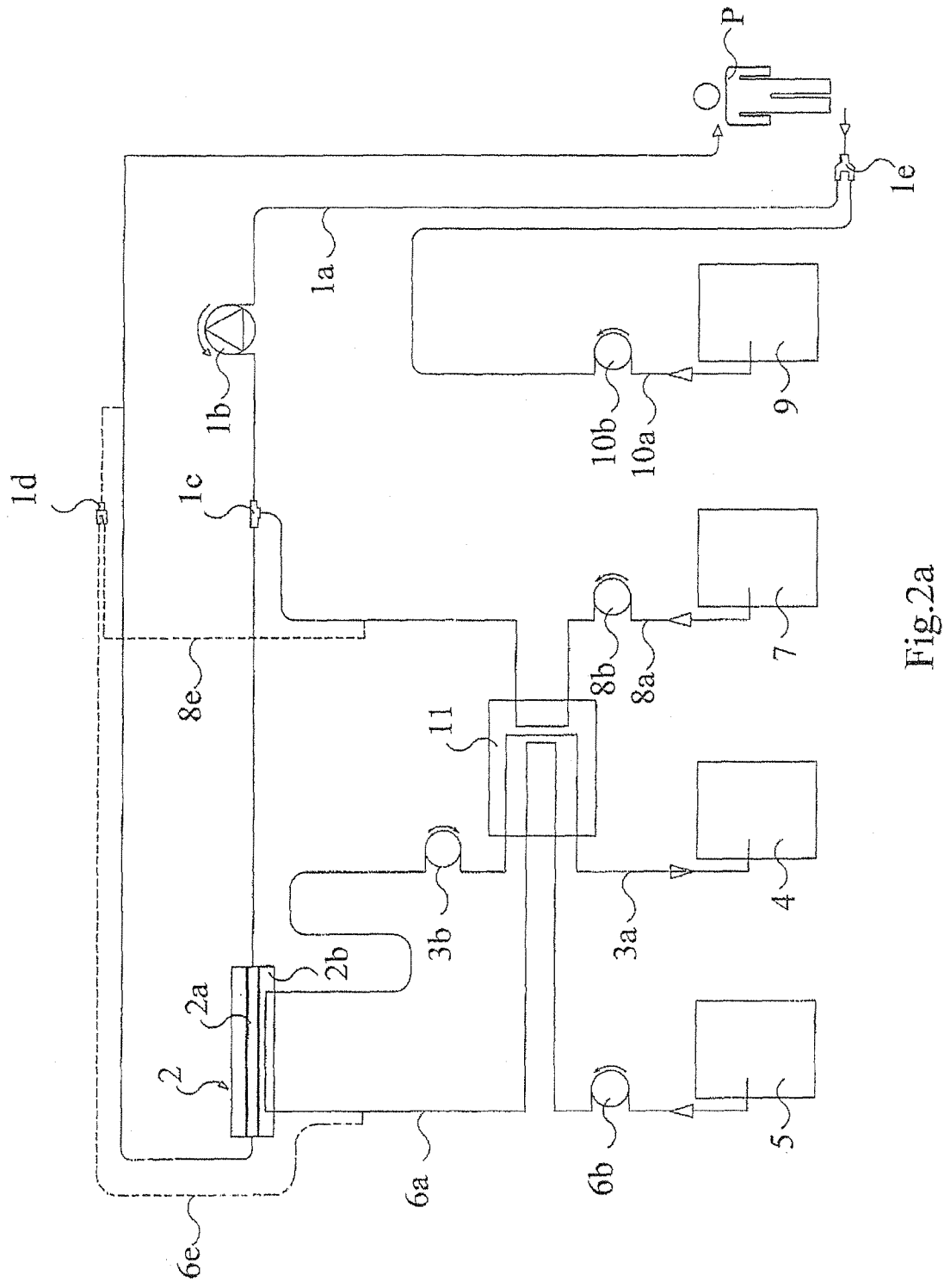
FIG. 2a schematically illustrates a CRRT flow diagram comprising a heat exchanger for exchanging heat between one primary fluid and two secondary fluids.

FIG. 2a shows a schematic view of a CRRT arrangement, initially described in connection with FIG. 1, comprising a heat exchanger 11 suitable for heating at least a first and optionally also a second secondary fluid by means of one primary fluid. The primary fluid may be the effluent fluid extracted from the filtration unit 2 and the first secondary fluid may be the fresh dialysis fluid stored in the dialysis fluid source 5 and the second secondary fluid may be a replacement fluid stored in the replacement fluid source 7. Alternatively a replacement fluid is stored also in fluid source 5.

Figure 2B:
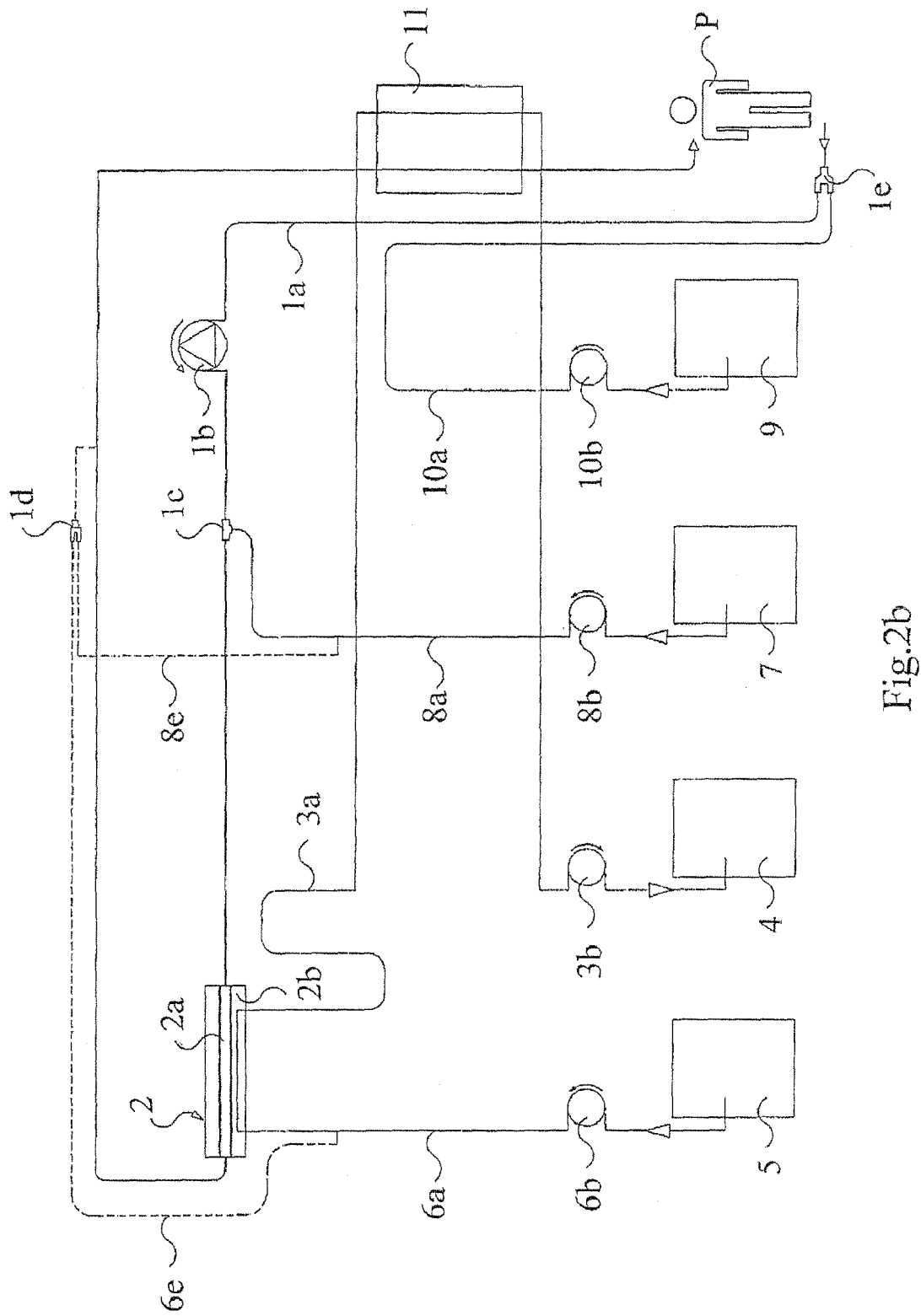
FIG. 2b schematically illustrates a CRRT flow diagram comprising a heat exchanger for exchanging heat between one primary fluid and blood.

FIG. 2b shows a schematic view of a CRRT arrangement, initially described in connection with FIG. 1, comprising a heat exchanger 11 suitable for heating blood by means of one primary fluid. The primary fluid may be the effluent fluid extracted from the filtration unit 2. The heat exchanger may be of plate type or hollow fiber type where the hollow fibers may be of semipermeable or non permeable type.

Figure 3A:
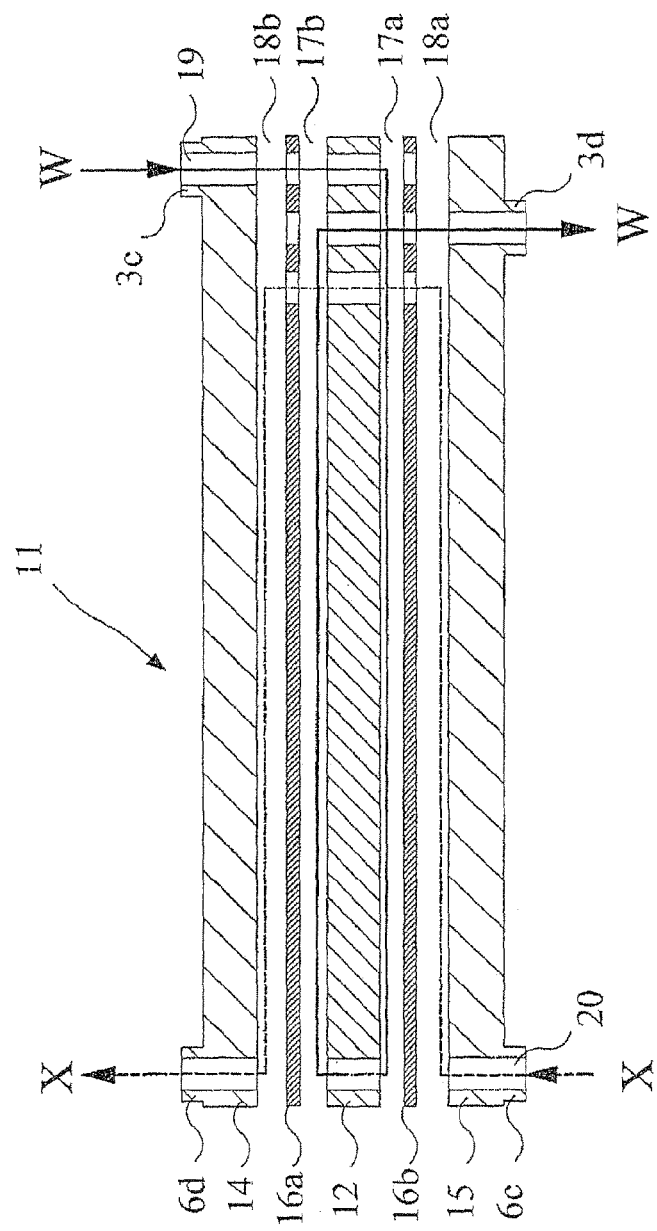
FIG. 3a schematically illustrates a principle for a two circuit heat exchanger with two heat transferring membranes in a principal cross sectional view.

In FIG. 3a is shown an embodiment of the principle of the internal structure of the heat exchanger 11. In this embodiment is comprised a first and a second secondary fluid plate in the form of end plates 14, 15 and a primary fluid plate 12 arranged therebetween. The fluid plates 12, 14, 15 are substantially thermally isolating. Membranes 16 are arranged intermediate the plates 12, 14, 15. A first fluid circuit 19 is adapted for passage of a primary fluid W and a second fluid circuit 20 is adapted for passing a secondary fluid X such that heat exchange between the primary fluid W and the secondary fluid X takes place over each of the thermally conductive membranes 16.

In use the primary fluid W enters, according to the orientation shown, the heat exchanger 11 via the first inlet port 3c at the upper right end. The primary fluid W is passed through the first end plate 14, the first membrane 16a and the primary fluid plate 12 to a first interspace for primary fluid 17a. The primary fluid W is then passed in the first interspace 17a from the right in the FIG. 3a to the left and through the primary fluid plate 12 to the second interspace for primary fluid 17b. The primary fluid W is then passed in the second interspace 17b from the left in the FIG. 3a to the right and through the primary fluid plate 12, the second membrane 16b, through the second endplate 15 and out through the first outlet port 3d.

In the embodiment shown the primary fluid W and the secondary fluid X are arranged to flow in a counter current direction. The secondary fluid X is heated by means of the primary fluid W over two separate heat exchanging surfaces, i.e. membranes 16a, 16b.

Simultaneously, the secondary fluid X is let in through the second inlet port 6c arranged at the lower left side of the heat exchanger 11 and through the second end plate 15 to the first interspace for secondary fluid 18a. The secondary fluid X is then passed in the first interspace 18a from the left side in the FIG. 3a to the right and through the second membrane 16b, the primary fluid plate 12, the first membrane 16a to the second interspace for secondary fluid 18b. The secondary fluid X is then passed inte the second interspace 18b from the right in the FIG. 3a to the left and through the first end plate 14 and out through the second outlet port 6d.

Figure 3B:
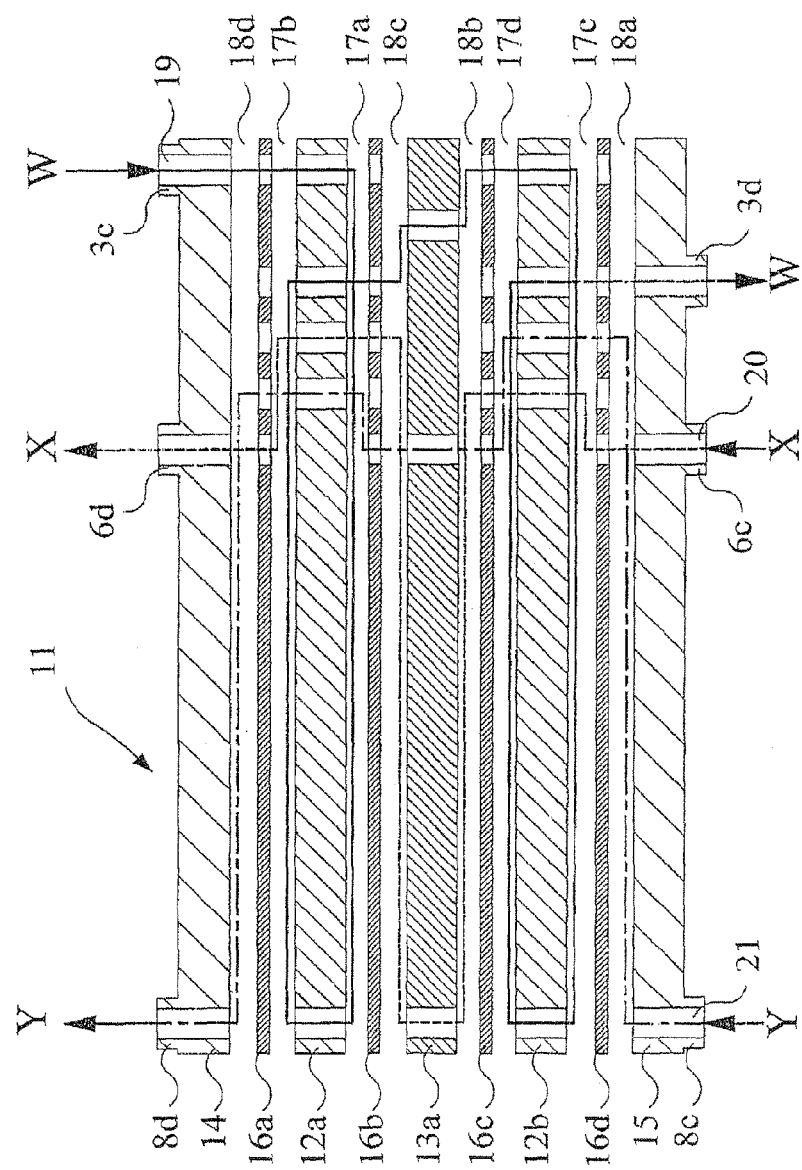
FIG. 3b schematically illustrates a principle for a three circuit heat exchanger with four heat transferring membranes in a principal cross sectional view.

In FIG. 3b is shown an embodiment of the principle of the internal structure of the heat exchanger 11 for a CRRT arrangement according to FIG. 2a. The heat exchanger 11 has three separate fluid circuits, i.e. a first, a second and a third fluid circuit 19, 20, 21 for a primary fluid W and a first and a second secondary fluid X, Y. According to the orientation of the principle shown in FIG. 3b, the internal structure comprises a package of plates 12-15 where the plates are stacked on top of each other with a membrane 16 arranged between each plate. The membranes 16 are fluid tight and non-permeable. The membranes will hereinafter generally be referred to as membranes 16 and for detailed reference provided with an accompanying letter 16a, 16b, 16c etc.

The plates are of a first and a second design respectively. The plate of the first design is designed for passing the primary fluid W on its upper and lower side and for passing primary fluid W through the same. The plates of the first design will hereinafter generally be referred to as primary fluid plates 12 and for detailed reference provided with an accompanying letter 12a, 12b, 12c etc. The plate of the second design is designed for passing the respective secondary fluids X, Y on its upper and lower side and for passing the secondary fluid X, Y through the same. The plates of the second design will hereinafter generally be referred to as secondary fluid plates 13 and for detailed reference provided with an accompanying letter 13a, 13b, 13c etc.

The primary fluid plates 12 and the secondary fluid plates 13 are arranged in an alternating order between a first end plate 14 and a second end plate 15. The first and the second end plate 14, 15, being a further type of fluid plate, has at least one side designed for passing a primary or a secondary fluid W, X, Y.

In FIG. 3b the plates 12, 13, 14, 15 and the membranes 16 are for the sake of clarity shown in a position where they are retracted from each other.

The plates 12-15 and membranes 16 have a generally rectangular form and a uniform outside dimension and the peripheries of adjacent plates are, via the intermediate membrane, connected in a fluid tight manner. In an alternative embodiment (not shown) the plates 12-15 and the membranes 16 may instead of the generally rectangular form have a generally octagonal form.

Each of the plates 12, 13, 14, 15 has at least one side provided with supporting ridges 23a, shown in FIGS. 5 and 6a, 6b, 7a, 7b, which together with the adjacent membrane 16 and adjacent plate form interspaces for passage of the fluids through the respective fluid circuit 19, 20, 21 through the heat exchanger 11. Thus, the heat exchange between the primary fluid W and the secondary fluids X, Y takes place over each of the membranes 16.

Figure 5:
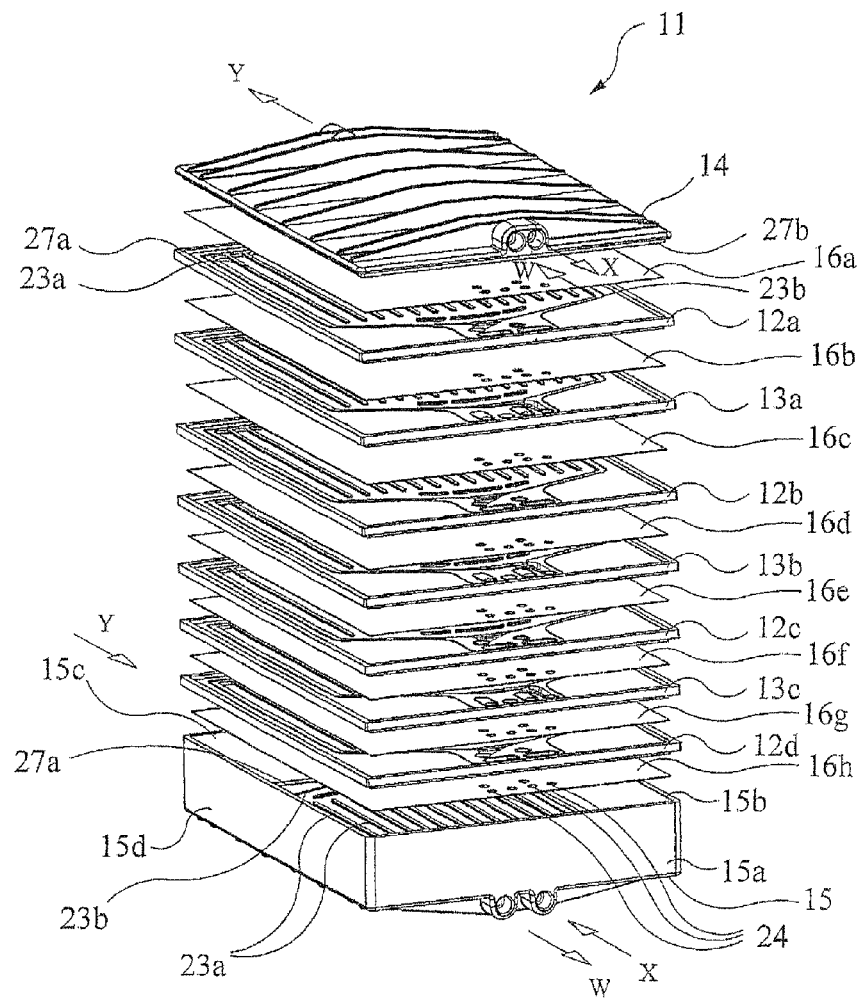
FIG. 5 illustrates the embodiment of the heat exchanger in FIG. 4 with the comprised components retracted from each other.

Each of the plates 12, 13 and at least one of the endplates 14, 15 has at least one side provided with sealing ridges 23b, shown in FIG. 5, 6a, 7a which together with the adjacent membrane 16 and adjacent plate provide a fluid tight seal between adjacent plates.

The interspace for delimitation of a flow passage for the primary fluid W will hereinafter generally be referred to as the interspace for primary fluid 17 and for detailed reference provided with an accompanying letter 17a, 17b, 17c etc. The interspace for delimitation of flow passages for the first or the second secondary fluid, X, Y will hereinafter generally be referred to as the interspace for secondary fluid 18 and for detailed reference provided with an accompanying letter 18a, 18b, 18c etc.

The principle embodiment of the internal structure of the heat exchanger 11 shown in FIG. 3b comprises a first inlet port 3c for inlet of the primary fluid W, and a first outlet port 3d for outlet of the same, a second inlet port 6c for inlet of a first secondary fluid X, a second outlet port 6d for outlet of the same, a third inlet port 8c for inlet of a second secondary fluid Y and a third outlet port 8d for outlet of the same. The ports are arranged such that the upper end plate 14 is provided with the first inlet port 3c and the second and the third outlet ports 6d, 8d and the lower end plate 14 is provided with the first outlet port 3d and the second and the third inlet ports 6c, 8c.

The first fluid circuit 19 is arranged connecting the first inlet port 3c and the first outlet port 3d. The second fluid circuit 20 is arranged connecting the second inlet port 6c and the second outlet port 6d. The third fluid circuit 21 is arranged connecting the third inlet port 8c and the third outlet port 8d. In futher detail the first fluid circuit 19 passes through the plates 12a-b, 13a, 14, 15 and the membranes 16a-d and along the interspaces for primary fluid 17a-d. The second and the third fluid circuits 20, 21 passes through the plates 12a-b, 13a, 14, 15 and the membranes 16a-d and along at least some of the interspaces for secondary fluid 18a-d

Each of the inlet and outlet ports 3c, 3d, 6c, 6d, 8c, 8d are attached to lines or the like (not shown) for delivery or withdrawal of fluids W, X, Y.

Thus, each of the the primary fluid plates 12a-b the first secondary fluid plate 13a, the end plates 14, 15 and the membranes 16*a-d* are provided with portions of the first, second and third fluid circuit 19, 20, 21 in the form of throughgoing ports 24, shown in FIGS. 5 and 6*a*, 6*b*, 7*a*, 7*b*, for allowing fluid passage. The interspaces 17, 18 formed between the respective side of a fluid plate 12-15 and a membrane 16 constitutes the heat changing portions of the respective fluid circuit 19, 20, 21, 28.

In use the embodiment of a heat exchanger 11 according to FIG. 3*b* allows the primary fluid W and the first and the second secondary fluids X, Y to flow in such a way that the primary fluid W alternatingly heats the first and the second secondary fluid X, Y.

In summary the primary fluid W passes over both sides of each of the two primary fluid plates 12*a*, 12*b* along its way through the first fluid circuit 19. The first secondary fluid X passes over both sides of one secondary fluid plate 13*a* along its way through the second fluid circuit 20. The second secondary fluid Y passes over one side of the respective first and second end plate 14, 15 along its way through the third fluid circuit 21.

The heat exchanger 11 has, according to the orientation shown in FIG. 3*b*, an upper and a lower end and a left and a right side. When the heat exchanger 11 according to the embodiment shown in FIG. 3*b* is in use, the primary fluid W is let in on the upper end of the heat exchanger through the first inlet port 3*c* to the right and passed via the first fluid circuit 19 through the first end plate 14, the first membrane 16*a* and the first primary fluid plate 12*a* to the first interspace for primary fluid 17*a*. The primary fluid is then passed along the first interspace for primary fluid 17*a* from the right in the FIG. 3*b* to the left and through the first primary fluid plate 12*a* to the second interspace for primary fluid 17*b* and along the second interspace for primary fluid 17*b* from the left in the FIG. 3*b* to the right. The primary fluid is then passed through the first primary fluid plate 12*a*, the second membrane 16*b*, the first secondary fluid plate 13*a*, the third membrane 16*c*, and the second primary fluid plate 12*b* to the third interspace for primary fluid 17*c*. The procedure is then repeated according to the above until the primary fluid exits the second end plate 15 through the first outlet port 3*d* on the lower, right end of the heat exchanger 11.

According to the embodiment shown in FIG. 3*b* the first secondary fluid X to be heated by the primary fluid W is let in through the second inlet port 6*c* at the lower, right end of the heat exchanger and passed via the second channel 20 through the second end plate 15, the fourth membrane 16*d*, the second primary fluid plate 12*b* and the third membrane 16*c* to the second interspace for secondary fluid 18*b*. The first secondary fluid X is then passed along the second interspace for secondary fluid 18*b* from the right in the FIG. 3*b* to the left and through the first secondary fluid plate 13*a* to the third interspace for secondary fluid 18*c* and along the third interspace for secondary fluid 18*c* from the left in the FIG. 3*b* to the right. The first secondary fluid is then passed through the second membrane 16*b*, the first primary fluid plate 12*a*, the first membrane 16*a*, the first end plate 14 and through the second outlet port 6*d* on the upper, right end of the heat exchanger 11.

According to the embodiment shown in FIG. 3*b* the second secondary fluid Y to be heated by the primary fluid W is let in through the third inlet port 8*c* on the lower, left end of the heat exchanger 11 and passed via the third channel 21 through the second end plate 15 to the first interspace for secondary fluid 18*a* and along the first interspace 18*a* from the left side in the FIG. 3*b* to the right side and then through the fourth membrane 16*d*, the second primary fluid plate 12*b*, the third membrane 16*c*, the first secondary fluid plate 13*a*, the second membrane 16*b*, the first primary fluid plate 12*a* and the first membrane 16*a*, to the fourth interspace for secondary fluid 18*d*. The second secondary fluid is then passed along the fourth interspace for secondary fluid 18*d* from the right in the FIG. 3*a* to the left and through the first end plate 14 whereafter it exits through the third outlet port 8*d* on the upper, left end of the heat exchanger 11.

According to the embodiment shown in FIG. 3*b* each secondary fluid X, Y is heated over two separate membranes 16 by means of the primary fluid flow W.

When the heat exchanger 11 according to the embodiment shown in FIG. 3*b* is in use the primary fluid W is arranged to flow in a direction countercurrent to the first and the second secondary fluids X, Y through separate but adjacent compartments in the form of the interspaces 17, 18 for primary fluid and for secondary fluid respectively. I.e. the primary fluid in one interspace e.g. 17*d* flows through the heat exchanger 11 in a direction opposite to the flow of the secondary fluid in an adjacent interspace, 18*b*. The invention is however also applicable to a concurrent flow configuration.

The fluid flow, of at least one of the primary fluid W and the secondary fluid X, Y, is mostly laminar. Some turbulence is created in the flow in the area of passage of a fluid W, X, Y from one side of a plate 12-15 to the opposite side of the same plate.

Figure 3C:
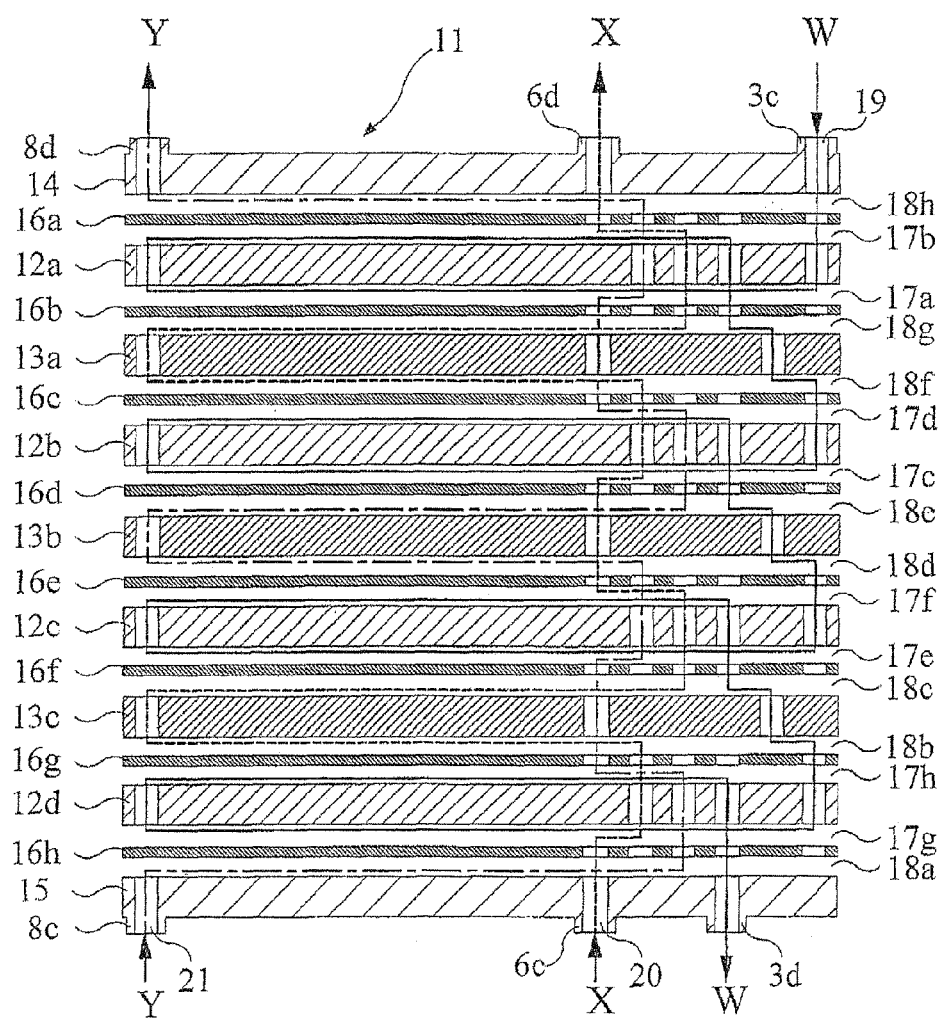
FIG. 3c schematically illustrates a principle for a three circuit heat exchanger with eight heat transferring membranes in a principal cross sectional view.

In FIG. 3*c* is shown an embodiment with an increased number of heat exchanging areas, i.e. membranes 16. More precisely the heat exchanging areas are eight instead of four as shown in FIG. 3*b*. The number of primary fluid plates 12 and secondary fluid plates 13 are increased accordingly. The principle corresponds to the one described in connection with FIG. 3*b* and the same reference numbers have been used for corresponding features. According to the embodiment shown in FIG. 3*c* each secondary fluid X, Y is heated over four separate membranes 16.

In the embodiment of the heat exchanger 11 shown in FIGS. 3*b* and 3*c* the primary fluid is arranged to heat a secondary fluid, e.g. a first secondary fluid X in every second layer of primary and secondary plates 12, 13. The flow circuits 19, 20, 21 of the primary fluid W and the first and the second secondary fluids X, Y are interlaced such that the primary fluid W on one side of a primary plate 12 heats the first secondary fluid X and on the other side of the same primary plate heats the second secondary fluid Y.

The embodiment shown in FIG. 3*c* has, when using details of dimensions corresponding to those used for the embodiment shown in FIG. 3*b* a higher efficiency than the embodiment shown in FIG. 3*b* as the heat transfer area is increased. When designing a heat exchanger according to the above principle for a specific application the heat transfer area and the required efficiency has to be balanced.

Figure 4:
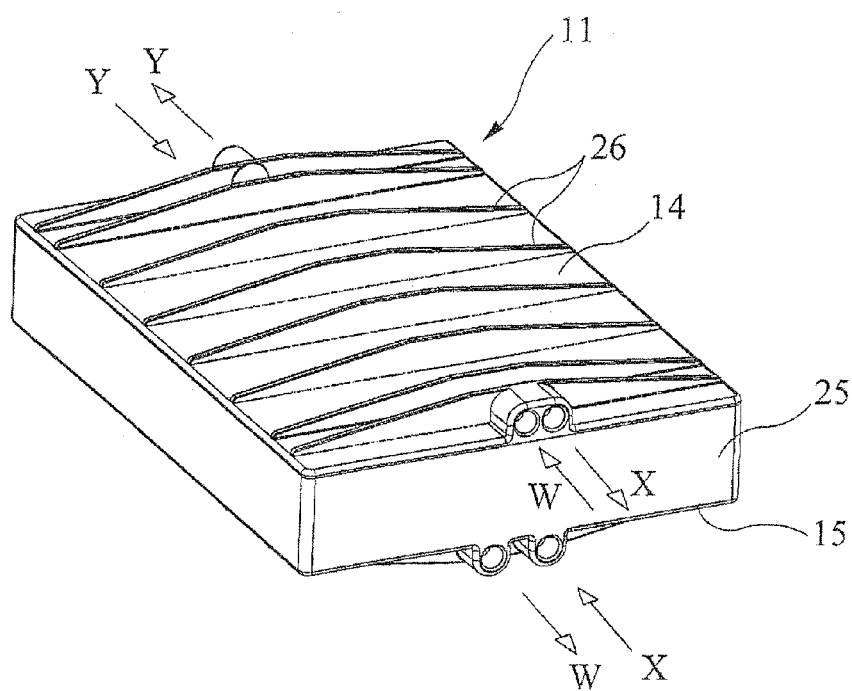
FIG. 4 illustrates one embodiment of a three circuit heat exchanger.

In assembly the package of plates 12, 13, 14, 15 and membranes 16 may be arranged in a housing, 25 according to FIG. 4. The housing 25 may be provided with reinforcing fins 26. An embodiment of a housing 25 is shown in more detail in FIG. 5.

In FIG. 5 is shown an exemplary heat exchanger 11 based on the principles shown in FIG. 3*c*. In FIG. 5 the heat exchanger 11 is shown in perspective view and with the comprised components retracted. The reference numbers used correspond to those used in connection with FIG. 3*c*. The components will be described in further detail in connection with FIGS. 5-8.

The housing 25 according to this embodiment is constituted with the first and the second end plates 14, 15 being integrated parts. More specifically the housing 25 in one embodiment is constituted by the second endplate 15 provided with side walls 15*a-d* for connecting with the first end plate 14. The walls 15a-d may be connected with the first end plate 14 by means of e.g. welding, moulding or gluing. Alternatively the walls 15a-d may be connected with the first end plate 14 by means of a fixation structure (not shown).

Figure 6A:
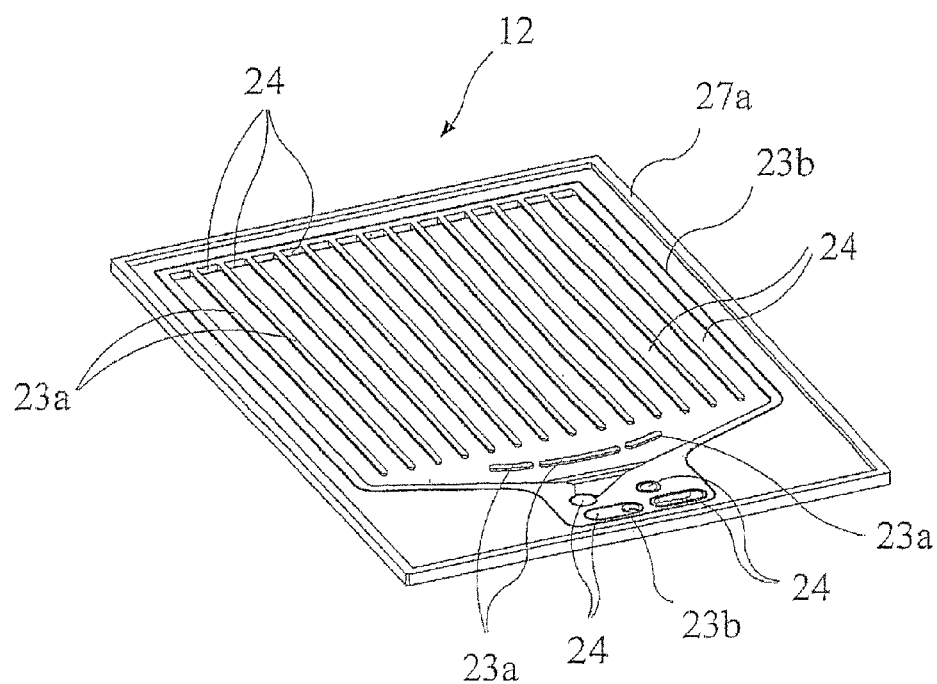
FIG. 6a, 6b illustrates an embodiment of a primary fluid plate of the type shown in FIG. 5.
Figure 6B:
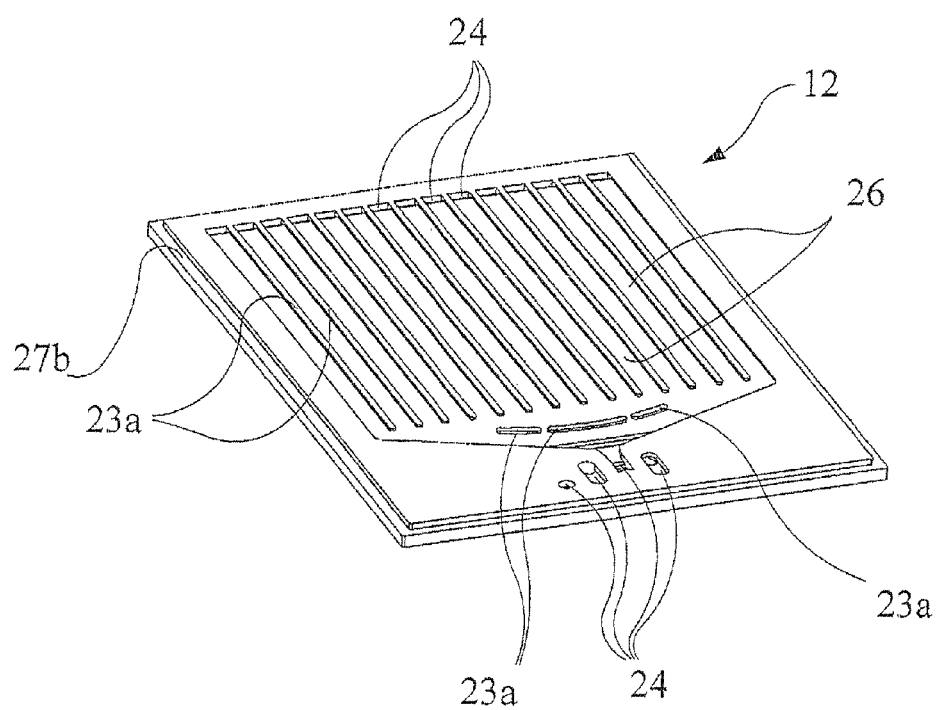
Figure 7A:
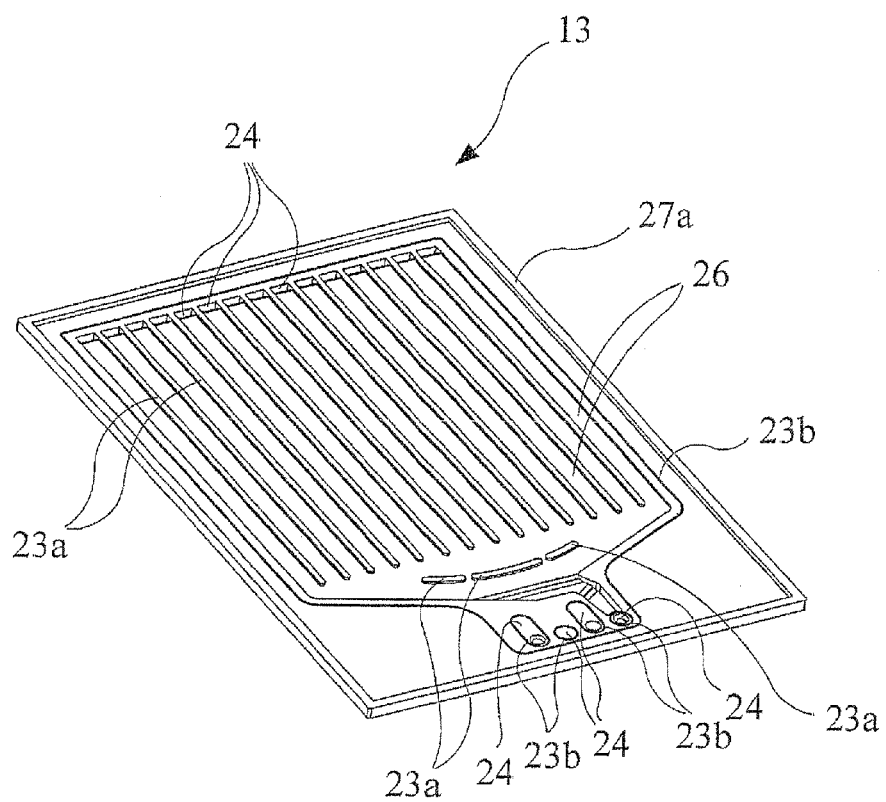
FIG. 7a, 7b illustrates an embodiment of a secondary fluid plate of the type shown in FIG. 5.
Figure 7B:
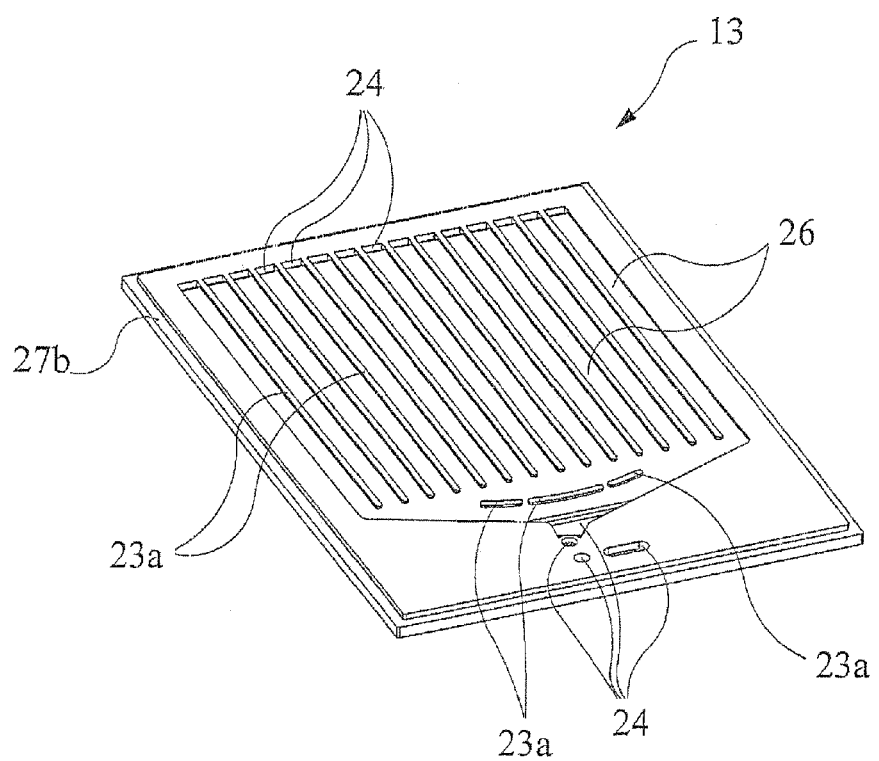

An example embodiment of the primary fluid plate 12 is shown in further detail in FIGS. 6a, 6b. An example embodiment of the secondary fluid plate 13 is shown in further detail in FIGS. 7a, 7b.

Each primary and secondary fluid plate 12, 13 is on each side, i.e. on the upper and the lower side, provided with channels 24 provided between the supporting ridges 23a. The channels 24 together form the primary and secondary fluid interspaces 17, 18. One side of the respective plate 12, 13 is also provided with a piling ridge 27a along its perimeter mating with a piling recess 27b on an adjacent plate 12, 13 such that the plates 12, 13 when piled are placed in a fixed position. The respective end plate 14, 15 is on one of its sides provided with corresponding supporting ridges 23a and piling ridges 27a or piling recesses 27b, indicated in FIG. 5. Further, each primary and secondary fluid plate 12, 13 is provided with a plurality of through going ports 24.

The supporting ridge 23a on the primary fluid plate 12 and the corresponding supporting ridge 23a on the adjacent secondary fluid plate 13 or on either of the endplates 14, 15 are arranged to face each other and to cooperate. Generally at least one side of the primary and secondary plates 12, 13 are provided with supporting ridges 23a having a flow distributing function or a flow collecting function. The supporting ridges 23a on two adjacent plates 12, 13, 14, 15 cooperate such that the flexible membrane 16 between the plates 12, 13, 14, 15 is supported in a position between the plates 12, 13, 14, 15. Thus, the membrane 16 is prevented from deflecting and thereby restraining the flow of the primary fluid W or any of the secondary fluids X or Y.

At least one side of each of the primary and secondary plates 12, 13 is provided with sealing ridges 23b. The sealing ridges extend such as to enclose the fluid carrying part of the respective plate and optionally also around the through going ports 24. Sealing between a membrane 16 and the sealing ridges 23b of the respective adjacent plates 12, 13 is provided when the plates 12, 13, and membranes 16 are arranged on top of each other and pressed together between the end plates 14, 15. At least the lower end plate 15 is provided with a sealing ridge 23b sealing against the fourth primary plate 12d via the membrane 16h (see FIG. 5). In this way adjacent plates 12-15 are connected in a fluid tight manner.

The end plates 14, 15 may be more rigid than the primary fluid plates 12 and the secondary fluid plates 13.

The first, second and third fluid circuit 19, 20, 21 respectively, are arranged at the respective right and left side of the heat exchanger in order to provide as large an area as possible for fluid carrying and thereby heat transfer.

Figure 8:
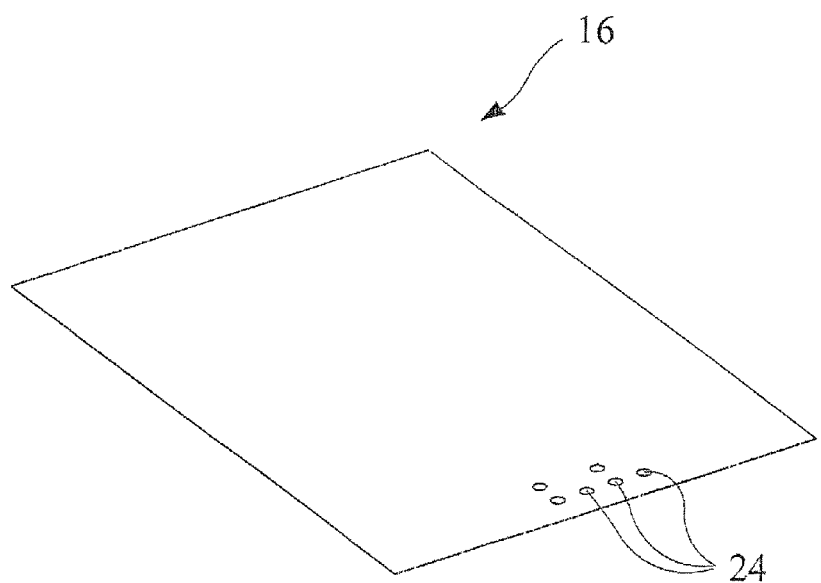
FIG. 8 illustrates an embodiment of a membrane of the type shown in FIG. 5.

In FIG. 8 is shown an example of an embodiment of a membrane 16 with a plurality of through going ports 24 that is used in the heat exchanger 11 shown in FIG. 5.

The supporting ridges 23a, sealing ridges 23b, channels 26, piling ridges 27a and piling recesses 27b may be designed in a wide range of different patterns.

The membranes 16 may be punched from a physiologically acceptable and flexible film material with relevant heat transfer coefficient such as High Density or Low Density Polyethylene or laminated Polyethylene.

The primary fluid plates 12 and the secondary fluid plates 13 may be manufactured by means of injection-moulding in a physiologically acceptable material such as Low Density Polyethylene (LDPE).

The housing may be manufactured in e.g. Polycarbonate (PC), Styrene-Acrylonitrile (SAN), Thermoplastic Polyurethane or Acrylonitrile-Butadiene-Styrene (ABS).

As mentioned above the heat exchanger 11 may be disposable. However, the materials for the components of the heat exchanger 11 may be chosen such that the heat exchanger 11 may be cleaned or disinfected and reusable.

Figure 9:
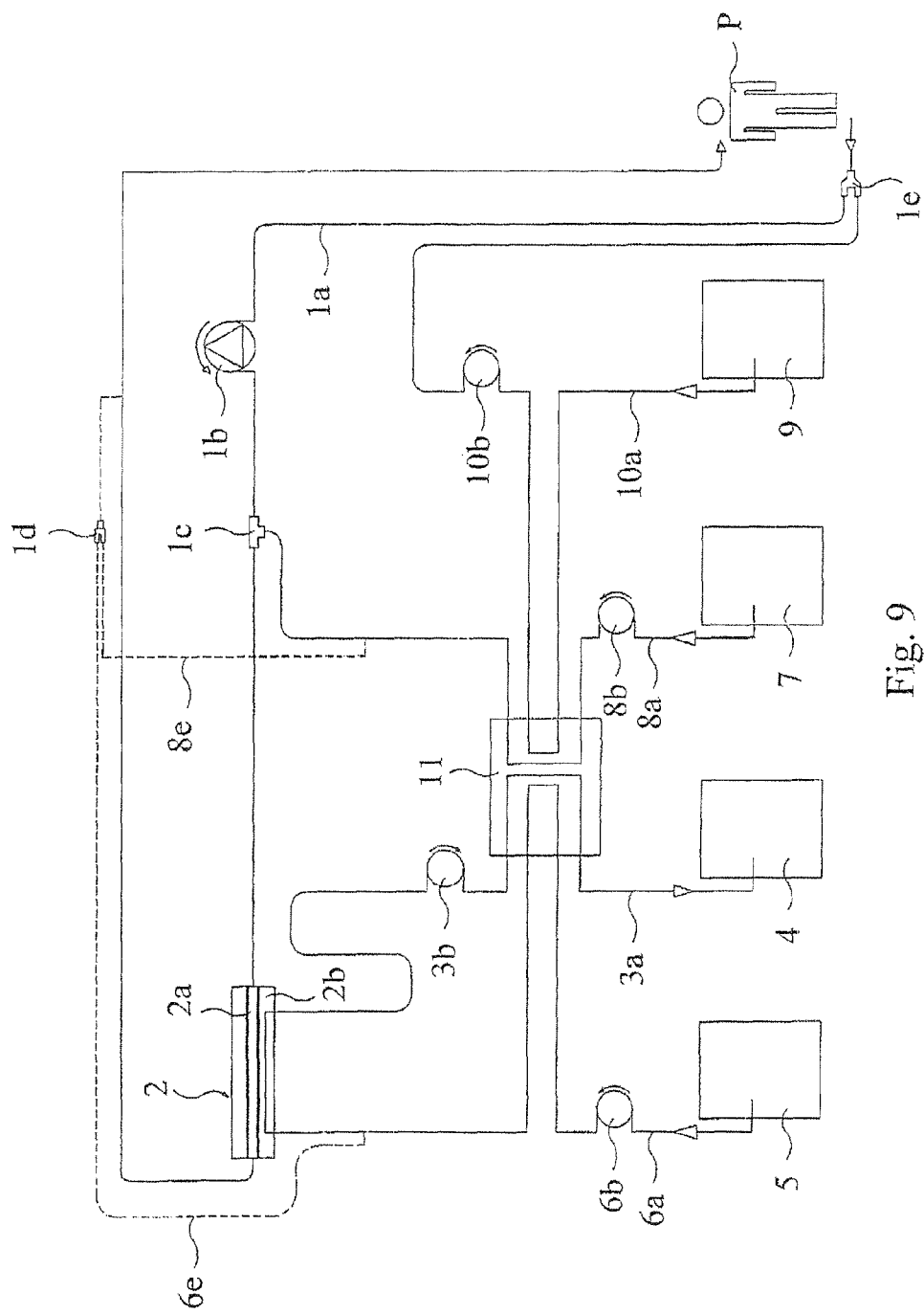
FIG. 9 schematically illustrates a CRRT flow diagram comprising a heat exchanger for exchanging heat between one primary fluid and three secondary fluids.

FIG. 9 shows a schematic view of a CRRT arrangement comprising a heat exchanger 11 suitable for heating a first, a second and a third secondary fluid X, Y, Z by means of one primary fluid W. The primary fluid W may be the effluent fluid extracted from the filtration unit 2 and the first secondary fluid X may be the fresh dialysis fluid stored in the dialysis fluid source 5, the second secondary fluid Y, may be a replacement fluid stored in the replacement fluid source 7 and the third secondary fluid Z may be an anticoagulant fluid from an anticoagulation fluid source 9.

Figure 10A:
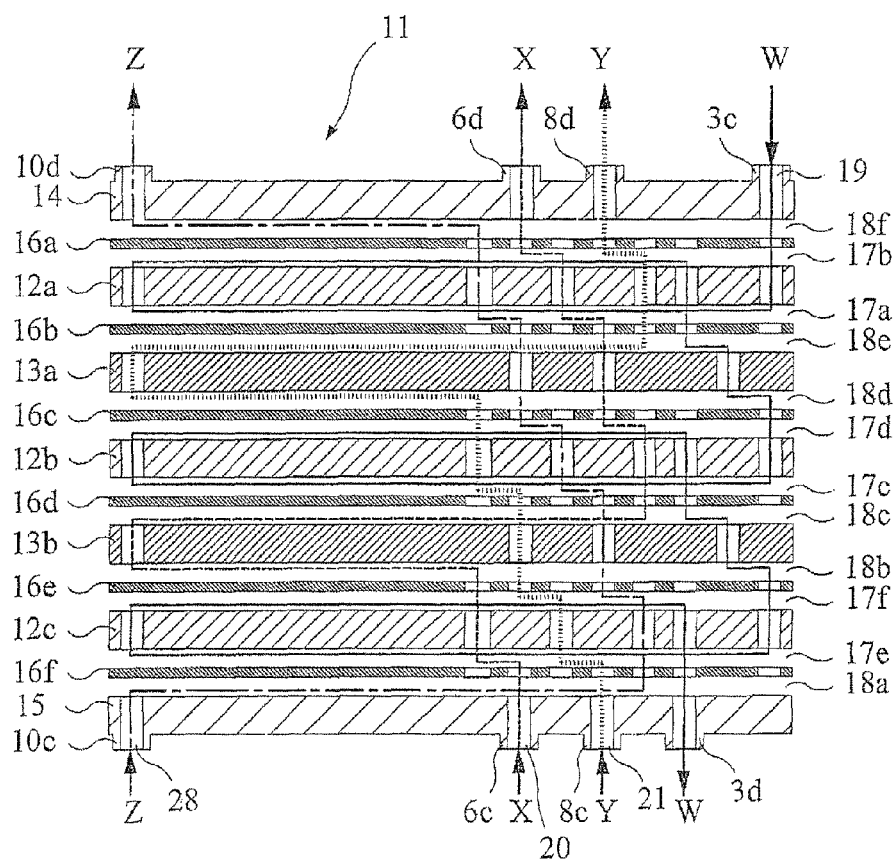
FIG. 10a schematically illustrates a principle for a four circuit heat exchanger with six heat transferring surfaces in a principal cross sectional view.

In FIG. 10a is shown an embodiment of the principle of the internal structure of the heat exchanger 11 for a CRRT arrangement according to FIG. 9. The principle shown in FIG. 10a comprises four separate fluid circuits 19, 20, 21 and 28 for heat exchange between a primary fluid W and three secondary fluids X, Y, Z. Components corresponding to those shown in FIG. 3a, 3b have been given the corresponding reference numbers. Further the heat exchanger 11 comprises a fourth inlet port 10c for inlet of third secondary fluid Z, and a fourth outlet port 10d for outlet of the same. The principle shown in FIG. 10a comprises six heat transferring areas, i.e. membranes 16, three primary fluid plates 12 and two secondary fluid plates 13 and a top plate 14 and a bottom plate 15.

According to the embodiment of a heat exchanger 11 according to FIG. 10a the primary fluid flow W is arranged to alternatingly heat the first, the second and the third secondary fluid X, Y, Z.

In summary the primary fluid W passes over three primary fluid plates 12a, 12b, 12c along its way through the first fluid circuit 19. The first secondary fluid X passes over both sides of one secondary fluid plate 13b along its way through the second fluid circuit 20. The second secondary fluid Y passes over both sides of one secondary fluid plate 13a along its way through the third fluid circuit 21. The third secondary fluid Z passes over one side of the respective first and second end plate 14, 15 along its way through the third fluid circuit 28.

The embodiment in FIG. 10a shows that the primary fluid W is arranged to flow in one interspace e.g. 17a between a second membrane 16b and a first primary fluid plate 12a in a direction opposite to the flow of the primary fluid in an interspace, 17b arranged on the other side of the same primary fluid plate 12a. In addition the secondary fluids X, Y, Z are arranged to be heated alternatingly such that the heat from the primary fluid W is distributed more evenly between the respective secondary fluid X, Y, Z than if the secondary fluids had been heated one after the other (i.e. not alternatingly). The alternating way of heating the secondary fluids is also more efficient since a larger fraction of the heat in the primary fluid W is transferred to the secondary fluids X, Y, Z. The alternating way of heating the respective secondary fluid X, Y, Z results in that the temperature difference between the primary fluid W and any of the secondary fluids X, Y, Z is maximized through the complete heat exchanger 11, i.e. the primary fluid W more or less heats each secondary fluid X, Y, Z to the same extent. According to the embodiment shown in FIG. 10a each secondary fluid X, Y, Z is heated over two separate membranes 16.

Figure 10B:
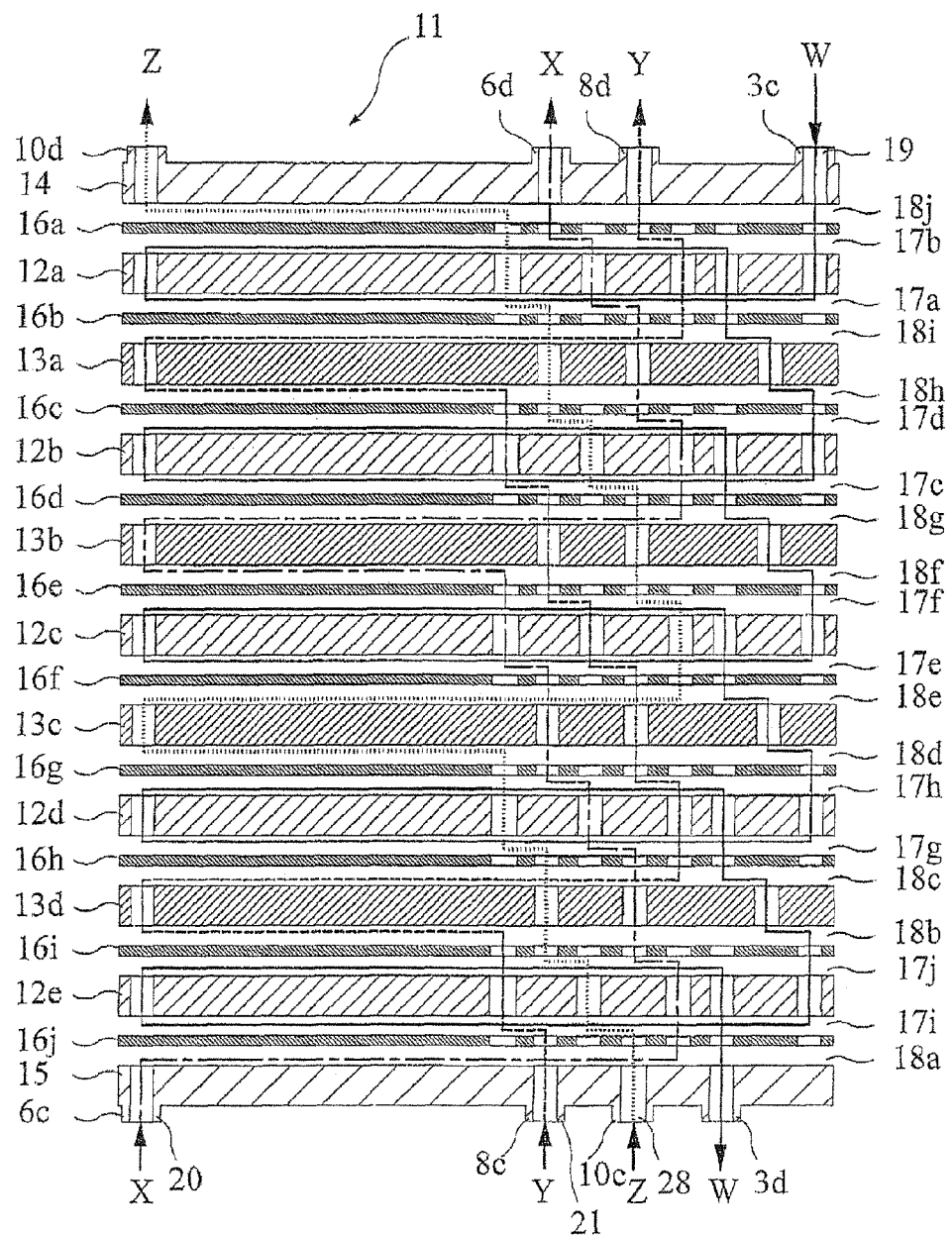
FIG. 10b schematically illustrates a principle for a four circuit heat exchanger with ten heat transferring surfaces in a principal cross sectional view.

In FIG. 10b is shown an embodiment with an increased number of heat exchanging areas, i.e. membranes 16. More precisely the heat exchanging areas are ten instead of six as shown in FIG. 10a. The number of primary fluid plates 12 and secondary fluid plates 13 are increased accordingly. The principle corresponds to the one described in connection with FIG. 10a and the same reference numbers have been used for corresponding features. According to the embodiment shown in FIG. 10b the first and the third secondary fluid X, Z are heated over three separate membranes 16 and the second secondary fluid Y is heated over four separate membranes 16.

In the embodiment shown in FIGS. 3b, 3c, 10a and 10b the primary fluid W is let in from the top of the heat exchanger 11 and the secondary fluids X, Y, Z are let in from the bottom of the heat exchanger 11. The suggested design shown in FIGS. 3a, 3b, 10a and 10b results in the flow direction of the primary fluid W and any secondary fluid X, Y, Z being counter current. It also results in that the heat transferring membranes 16 close to the respective outlet 6d, 8d, 10d for the secondary fluids X, Y, Z are heated by a warmer primary fluid W than the membranes closer to the inlet for the secondary fluids 6c, 8c, 10c. In this way the heat energy in the primary fluid W is utilized in an efficient way.

In the embodiment according to FIG. 3b, 3c, 10a, 10b the flow of primary fluid W on one side of a membrane 16 is counter current to any of the secondary fluids on the other side of the same membrane 16.

Heat transfer efficiency of the heat exchanger 11 is dependent on the material chosen for the membranes 16, as well as the thickness of the material, the width, depth and length of the flow path and the area available for heat transfer. Consideration of heat transfer efficiency, however, must be balanced with the unfavorable pressure drop through the heat exchanger 11.

An exemplary embodiment A of the heat exchanger 11 of the type shown in FIG. 10b having four fluid circuits 19, 20, 21, 28 and ten heat exchanging surfaces, i.e. membranes 16a-j, has the following dimensions and choice of material.

| Embodiment A | Width (mm) | Length (mm) | Height (mm) | Material |
|---|---|---|---|---|
| Primary plate 12 | 93.5 | 133 | 2.25 | LDPE |
| Secondary plate 13 | 93.5 | 133 | 2.25 | LDPE |
| Bottom plate 15 | 96.5 | 136 | 31.75 | PC |
| Top plate 14 | 96.5 | 136 | 9.25 | PC |
| Membrane 16 | 89 | 128.5 | 0.1 | Laminated PE |

The exemplified embodiment A is suitable for sterilizing with ETO.

Figure 11A:
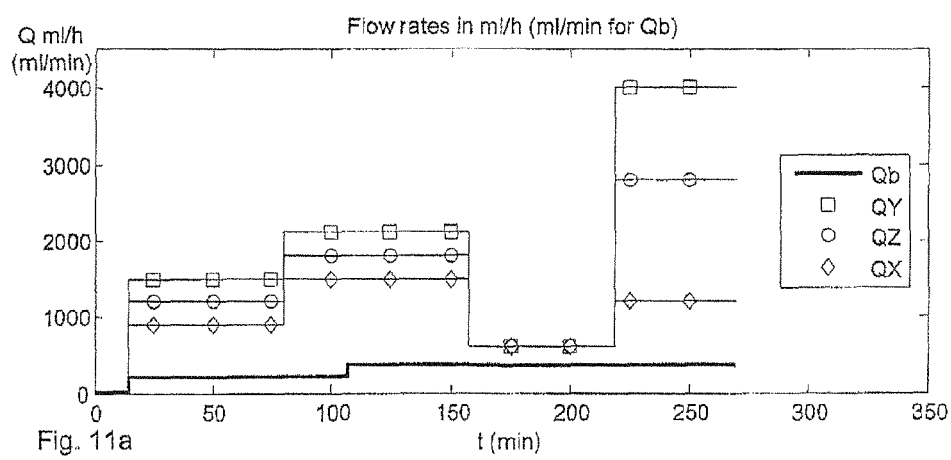
FIG. 11a-c show flow rates, temperatures and efficiency curves related to a tested heat exchanger of the type illustrated in FIG. 10b.
Figure 11B:
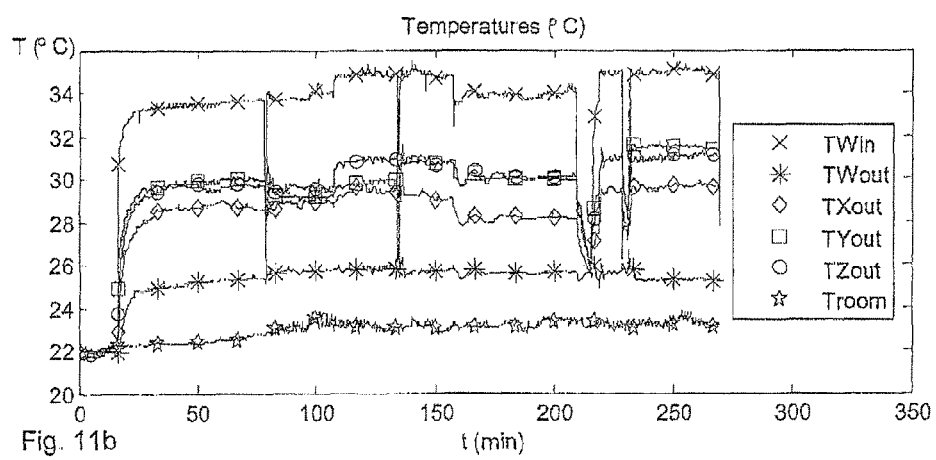
Figure 11C:
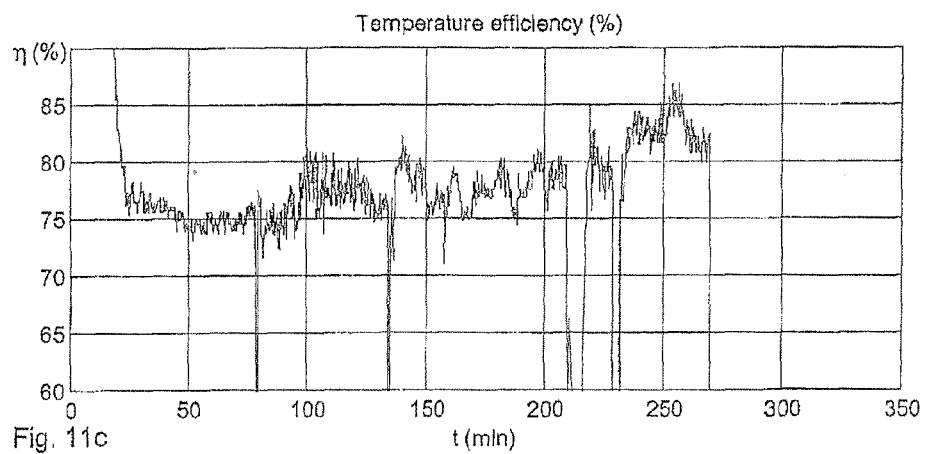

The exemplified embodiment A has been tested in an HDF treatment. Test results are shown in FIG. 11a-c. In FIG. 11a is shown a diagram where the y-axis indicates flow rates, Q in ml/hour for the primary and the secondary fluid flows into the heat exchanger 11 and in ml/minute for the extracorporeal blood flow rate Qb and the x-axis indicates the time, t in minutes. The diagram shows a treatment made in five different modules. The first module starts at 15 minutes and ends at 80 minutes. The second module starts at 80 minutes and ends at 105 minutes. The third module starts at 105 minutes and ends at 160 minutes. The fourth module starts at 160 minutes and ends at 220 minutes. The fifth module starts at 220 minutes and ends at 270 minutes. Replacement fluid and anticoagulant fluid is used in addition to the dialysis fluid. The flow of the respective fluid, i.e. flow of dialysis fluid, QY, flow of replacement fluid, QZ, and flow of anticoagulation fluid, QX varies between the modules. The effluent flow is not shown in the diagram but corresponds to the sum of the respective fluid flow, i.e. the sum of QY, QZ and QX, i.e. in the test there is no fluid removal from the blood. The extracorporeal blood flow, Qb varies between the first two and the last three modules. The curves in the diagram have the following references:
Qb=extracorporeal blood flow
QY=dialysis fluid flow
QZ=replacement fluid flow
QX=anticoagulant fluid flow In FIG. 11b is shown a diagram where the y-axis indicates temperature, T, in C.° and the x-axis indicates the time, t, in minutes. It is shown that the room temperature is about 23° C. (Troom) and the temperature of the effluent fluid is about 33-35° C. (TWin) when entering the heat exchanger 11 and about 25° C. (TWout) when it exits the heat exchanger 11. In this example the fresh dialysis fluid, the replacement fluid and the anticoagulant fluid all have room temperature when entering the heat exchanger 11. When these fluids are heated in the heat exchanger 11 they reach a temperature in the range of 27-31° C. In connection with change of treatment module there is a temporary disturbance in the temperature measurement. The curves in the diagram have the following references:
TWin=temperature of the effluent fluid, i.e. the primary fluid W entering the heat exchanger 11
TWout=temperature of the effluent fluid, W exiting the heat exchanger 11
TYout=temperature of the heated fresh dialysis fluid, Y when leaving the heat exchanger 11
TZout=temperature of the heated replacement fluid, Z when leaving the heat exchanger 11
TXout=temperature of the heated anticoagulant fluid, X when leaving the heat exchanger 11

In FIG. 11c is shown a diagram where the y-axis indicates temperature efficiency, η in % and the x-axis indicates time, t in minutes. It is shown how much of the increased temperature of the primary fluid W that is recovered, i.e. the heat exchanging efficiency. The heat exchanging efficiency, η varies mainly between 74 and 85% over the measured time period. In connection with change of treatment module there is a temporary disturbance in the efficiency measurement.

The suggested interlaced fluid circuits 19, 20, 21, 28 utilize the heat energy in the primary fluid W in a way that is more efficient than passing the primary fluid W through e.g. three separate heat exchangers of plate type arranged in series where one secondary fluid X, Y, Z is heated by the primary fluid W in each of the respective serially arranged heat exchangers 11.

The disclosed heat exchanger with three or four fluid circuits is suitable also for heating one secondary fluid only (e.g. X) by means of a primary fluid W. Thus only one of the fluid circuits 20, 21, 28 is filled with a secondary fluid and the other one or two fluid circuits is (are) empty.

In an alternative use of the three circuit heat exchanger 11 the method comprises the step of dividing the primary fluid W in two circuits to improve the heat transfer capacity to one secondary fluid. Alternatively the primary fluid W is the fluid to be heated by the secondary fluid.

In an alternative use of the four circuit heat exchanger 11 the method comprises the step of dividing the primary fluid W in three circuits to improve the heat transfer capacity to one secondary fluid. Alternatively the primary fluid W is the fluid to be heated by the secondary fluid.

In the above disclosed embodiments the first, second and third secondary fluids X, Y, Z are described as flowing in second, third and fourth fluid circuits 20, 21 and 28 respectively. However, the first secondary fluid X may as well flow in the third or fourth fluid circuit 21, 28 and the second secondary fluid Y may as well flow in the second or the fourth fluid circuit 21, 28 etc.

Figure 12:
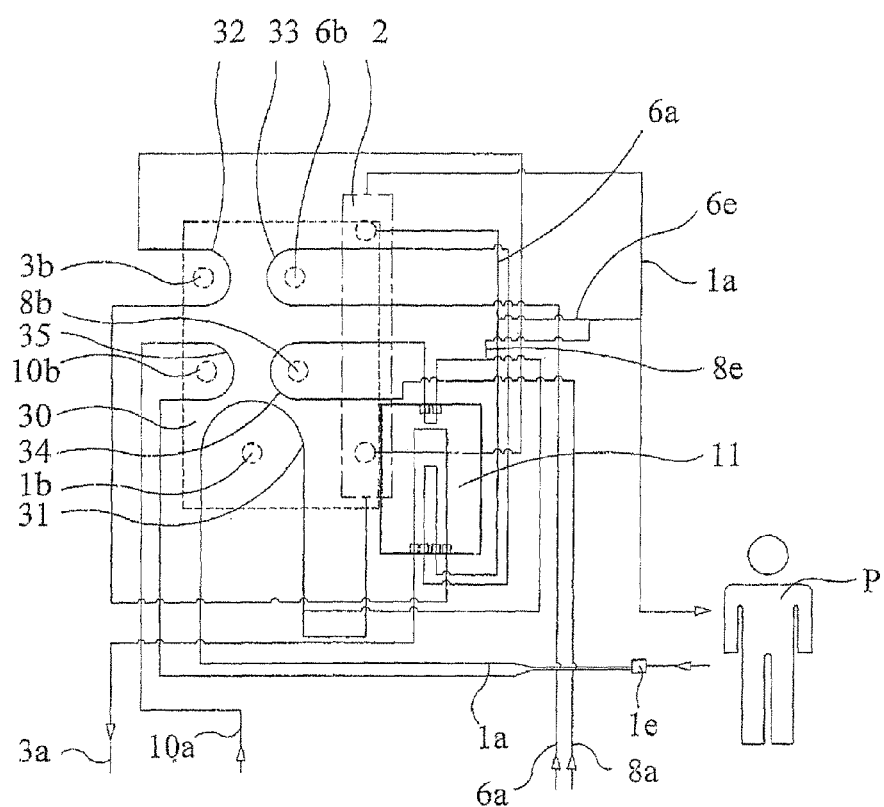
FIG. 12 schematically illustrates an embodiment of a disposable kit for a CRRT monitor comprising a heat exchanger of the type shown in FIG. 4.

In FIG. 12 is shown a principal sketch of a disposable kit in the form of an integrated fluid treatment module comprising a blood line 1a, and a fluid distribution circuitry comprising an effluent line 3a, multiple treatment fluid lines 6a, 8a, 10a and a heat exchanger 11 that is fluidly coupled to the effluent fluid line 3a and disposed in thermal relationship with the treatment fluid lines 6a, 8a, 10a so as to provide for transfer of heat from the effluent fluid to the treatment fluid. In one embodiment of the invention the heat exchanger 11 is one of the herein disclosed embodiments. The lines all have at least a portion forming a U-shaped line length 31, 32, 33, 34, 35 to cooperate with the respective pump, i.e. with the blood pump 1b, the effluent fluid pump 3b, the dialysis fluid pump 6b, the replacement fluid pump 8b and the anticoagulation fluid pump 10b. Optionally the disposable kit also comprises a filtration unit 2 associated with the blood line 1a and the fluid distribution circuitry. The lines 1a, 3a, 6a, 8a, 10a, the filtration unit 2 and the heat exchanger 11 are arranged on a support structure 50 indicated with dashed lines for facilitated connection of the lines to the pumps 1a, 3b, 6b, 8b, 10b.

Figure 13:
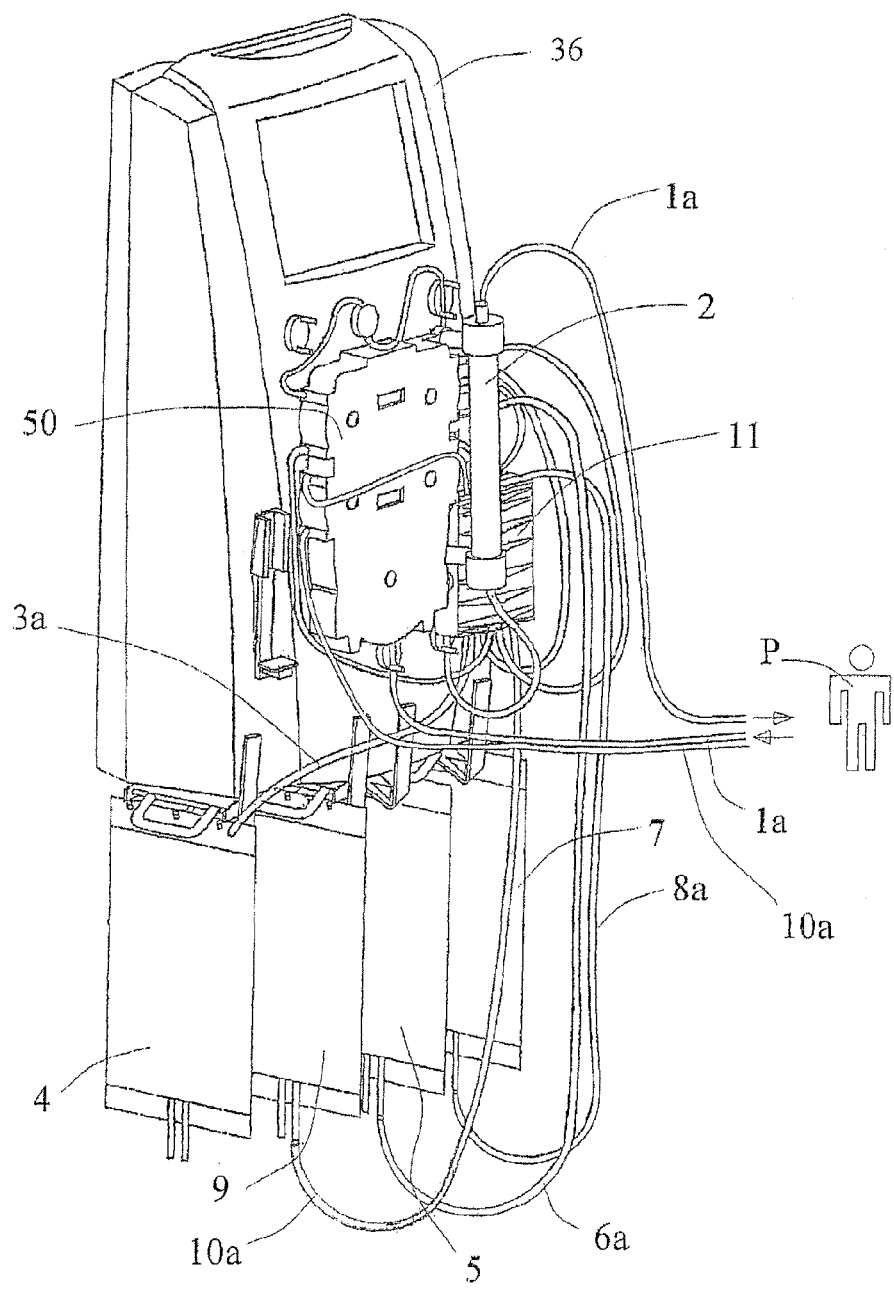
FIG. 13 schematically illustrates a kit according to FIG. 12 arranged on a CRRT monitor.

The disposable kit is designed to be used together with a CRRT machine of the type shown in FIG. 13. The disposable kit is in use arranged on a front side of a machine 36. The disposable kit has a blood line 1a, an effluent line 3a and a multiple of treatment fluid lines 6a, 8a, 10a. All the lines are associated to a support structure 50 and each line has a U-shaped portion 32 designed to cooperate with a respective pump 3b, 6b, 8b, 10b. A filtration unit 2 is also arranged on the support structure 50 and connected to the blood line 1a and to the dialysis fluid line 6a. Further the heat exchanger 11 is connected to the support structure 50 and fluidly coupled to the effluent fluid line 3a and disposed in thermal relationship with the treatment fluid line 6a, 8a, 10a so as to provide for transfer of heat from the effluent fluid to the treatment fluid.

Thus in use together with a CRRT machine, the heat exchanger 11 will be vertically arranged. Vertical arrangement of the heat exchanger 11 will facilitate air bubble dissipation. However, also arrangement in any other chosen position is feasible. In FIG. 13 is further indicated bags for containing effluent fluid 4, dialysis fluid 5, replacement fluid 7 and anticoagulant fluid 9.

Figure 14:
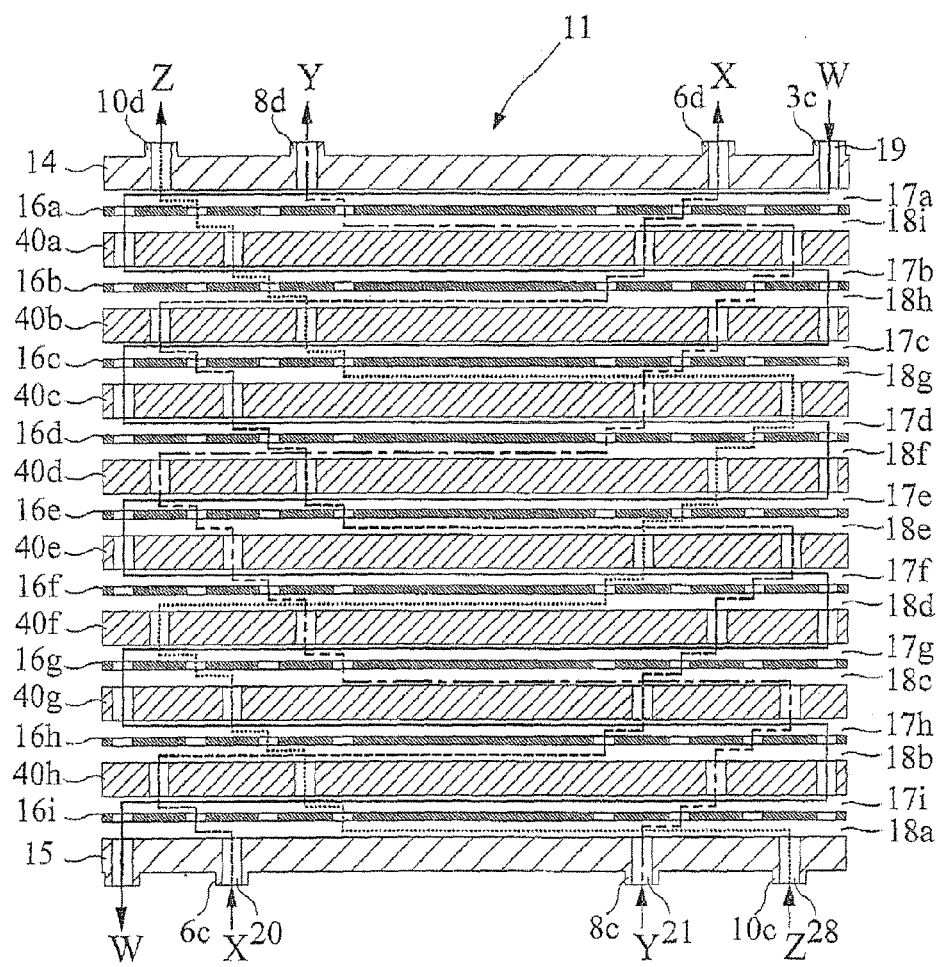
FIG. 14 schematically illustrates a principle for a four circuit heat exchanger with nine heat transferring membranes in a principal cross sectional view where the primary and secondary fluid plates are identical.

The principle of a further alternative embodiment is shown in FIG. 14. More specifically a four fluid circuit 19, 20, 21, 28 heat exchanger 11 is shown where all fluid plates 40 are equal. When stacking the plates 40 horizontally on top of each other every second fluid plate 40 is turned 180 degrees in a horizontal plane and in relation to the orientation of the adjacent fluid plates.

According to the embodiment shown in FIG. 14 each secondary fluid X, Y, Z is heated over three separate membranes 16.

According to the embodiment of a heat exchanger 11 according to FIG. 14 the primary fluid flow W is arranged to alternatingly heat a first, a second and a third secondary fluid X, Y, Z.

In the embodiment according to FIG. 14 the flow of primary fluid W on one side of a plate 40 is counter current to the flow of a secondary fluid on the other side of the same plate 40.

According to the embodiment shown in FIG. 14 the first secondary fluid X to be heated by the primary fluid W is let in through the second inlet port 6c at the lower, left end of the heat exchanger 11 and passed via the second channel 20 through the second end plate 15, the ninth membrane 16i, the eighth fluid plate 40h to the second interspace for secondary fluid 18b. The first secondary fluid X is then passed along the second interspace for secondary fluid 18b from the left in the FIG. 14 to the right and through the eighth membrane 16h, through the seventh fluid plate 40g, the seventh membrane 16g, the sixth fluid plate 40f, fifth membrane 16f, fifth fluid plate 40e and to the fifth interspace for secondary fluid 18e. The first secondary fluid X is then passed along the fifth interspace for secondary fluid 18e from the right in the FIG. 14 to the left and through the fifth membrane 16e, the fourth fluid plate 40d, the fourth membrane 16d, the third fluid plate 40c, the third membrane 16c, second fluid plate 40b to the eighth interspace for secondary fluid 18h. The first secondary fluid X is then passed along the eighth interspace for secondary fluid 18h from the left in the FIG. 14 to the right and through the second membrane 16b, the first fluid plate 40a, the first membrane 16a, the first end plate 14 and through the second outlet port 6d on the upper, right end of the heat exchanger 11.

Corresponding fluid passages are true for the primary fluid W and the second and third secondary fluids Y, Z and disclosed in the exemplary embodiment in FIG. 14.

FIGS. 3a, 3b, 3c, 10a, 10b and 14 all show a principle for a heat exchanger where parts of the respective fluid circuits 19, 20, 21, 28 in the plates 12-15, 40 in the form of openings 24 are all visible in the cross sectional plane shown even if they in practice are arranged in a plane different from the cross sectional plane shown.

The term "comprises/comprising" when used in this specification is taken to specify the presence of stated features, integers, steps or components. However, the term does not preclude the presence or addition of one or more additional features, integers, steps or components or groups thereof.

The reference to prior art in this specification is not, and should not be taken as, an acknowledgment or any suggestion that the referenced prior art forms part of the common general knowledge in Australia, or in any other country.

The invention is not restricted to the described embodiments in the figures, but may be varied freely within the scope of the claims.

The invention claimed is:

1. An arrangement for a continuous renal replacement therapy comprising:
 a continuous renal replacement monitor including at least one blood pump, and at least one treatment fluid pump;
 a disposable blood line associated with the monitor for extracorporeally circulating blood moved by the blood pump when connected to the blood line;
 a fluid distribution circuitry associated with the monitor comprising an effluent fluid line for passing effluent fluid;
 at least one line for a treatment fluid associated with the monitor for passing the treatment fluid and connectable to the treatment fluid pump to move the treatment fluid through the line, and
 a filtration unit arranged between the blood line and the fluid distribution circuitry, wherein the fluid distribution circuitry comprises a heat exchanger to be fluidly coupled to the effluent fluid line and disposed in thermal relationship with the at least one treatment fluid line to transfer of heat from the effluent fluid to the treatment fluid.

2. The arrangement according to claim 1 wherein the at least one line for treatment fluid is at least two lines and the heat is transferred from the effluent fluid to treatment fluid in the at least two lines.

3. The arrangement in the form of a disposable kit comprising
a support structure;
a blood line;
a fluid distribution circuitry comprising an effluent line and at least one treatment fluid line where the lines are associated to the support structure and the at least one treatment fluid line includes a U-shaped portion adapted to cooperate with a pump;
wherein the fluid distribution circuitry comprises a heat exchanger to be fluidly coupled to the effluent fluid line and disposed in thermal relationship with the treatment fluid line so as to provide for transfer of heat from the effluent fluid to the treatment fluid.

4. The arrangement according to claim 1 wherein the heat exchanger comprises a first fluid circuit and a separate second fluid circuit, a stack of fluid plates and a membrane arranged between each of the fluid plates where an interspace is formed between each fluid plate and the membrane opposite to the plate, and in that the first fluid circuit and the second fluid circuit each includes a respective passage extending through the fluid plates and the membranes and along the fluid plates and the membranes in at least two interspaces, and wherein at least one of the first and second fluid circuits extends from one side to an opposite side of the heat exchanger.

5. The arrangement according to claim 4 wherein the heat exchanger comprises a third fluid circuit separate from the first fluid circuit and the second fluid circuit where the third fluid circuit is constituted by a passage extending through the fluid plates and membranes and along the fluid plates and membranes in the at least two interspaces.

6. The arrangement according to claim 5 wherein the first fluid circuit is constituted by a passage extending in at least four of the interspaces.

7. The arrangement according to claim 5 wherein the first fluid circuit is constituted by a passage extending in at least eight of the interspaces, the second fluid circuit is constituted by a passage extending in at least four of the interspaces and the third fluid circuit is constituted by a passage extending in at least four of the interspaces.

8. The arrangement according to claim 5 wherein the heat exchanger comprises a fourth fluid circuit separate from the first fluid circuit, the second fluid circuit and the third fluid circuit, where the fourth fluid circuit is constituted by a passage extending through the fluid plates and the membranes and along the fluid plates and the membranes in at least two of the interspaces.

9. The arrangement according to claim 8 wherein the first fluid circuit is constituted by a passage extending in at least six of the interspaces.

10. The arrangement according to claim 8 wherein the first fluid circuit is constituted by a passage extending in at least ten of the interspaces, the second fluid circuit is constituted by a passage extending in at least three of the interspaces, the third fluid circuit is constituted by a passage extending in at least four of the interspaces and the fourth fluid circuit is constituted by a passage extending in at least three of the interspaces.

11. The arrangement according to claim 8 wherein the first fluid circuit is constituted by a passage extending in at least nine of the interspaces, the second fluid circuit is constituted by a passage extending in at least three of the interspaces, the third fluid circuit is constituted by a passage extending in at least three of the interspaces and the fourth fluid circuit is constituted by a passage extending in at least three of the interspaces.

12. The arrangement according to claim 4 wherein the fluid plates as well as the membranes are generally rectangular and each have a substantially similar outside shape and outside dimensions.

13. The arrangement according to claim 4 wherein the fluid plates and the membranes are generally octagonal and each have a substantially similar outside shape and outside dimensions.

14. The arrangement according to claim 4 wherein the fluid plates are divided into a group of primary fluid plates and a group of secondary fluid plates and where the primary fluid plates have a shape different from a shape of the secondary fluid plates.

15. The arrangement according to claim 11 wherein the fluid plates each have substantially similar shape.

16. The arrangement according to claim 15 wherein the fluid plates are divided into a first group and a second group where the fluid plates in the first group are oriented 180 degrees in a plane parallel with the fluid plates with respect to the fluid plates in the second group.

17. The arrangement according to claim 4 wherein the stack of fluid plates and membranes are arranged between an upper end plate and a lower end plate.

18. The arrangement according to claim 17 wherein the upper and lower endplates are integrated and form at least a portion of a housing.

19. The arrangement according to claim 4 wherein fluid plates have flow channels on opposite sides of the plates.

20. The arrangement according to claim 8 wherein each of the first, second, third and fourth fluid circuits are extending from one side of the heat exchanger to an opposite side of the heat exchanger.

21. The arrangement according to claim 4 wherein the fluid plates are substantially thermally isolating.

22. A method for exchanging heat between an effluent fluid and a treatment fluid in a heat exchanger according to claim 4, wherein the effluent fluid is passed through a first fluid circuit and the treatment fluid is passed through a second fluid circuit, the method comprises;
passing the effluent fluid along one side of a membrane and simultaneously passing the treatment fluid along another side of the membrane and exchanging heat between the effluent fluid and the treatment fluid over the membrane.

23. A method for exchanging heat between an effluent fluid and a first and a second treatment fluid in a heat exchanger according to claim 5, wherein the effluent fluid is passed through a first fluid circuit and the first treatment fluid is passed through a second fluid circuit and the second treatment fluid is passed through a third fluid circuit; the method comprises:
passing the effluent fluid along one side of a first membrane and simultaneously passing the first treatment fluid along another side of the first membrane and subsequently passing the effluent fluid along one side of a second membrane and simultaneously passing the second treatment fluid along another side of the second membrane, and
exchanging heat between the effluent fluid and the first treatment fluid over the first membrane, and exchanging heat between the effluent fluid and the second treatment fluid over the second membrane.

24. A method for exchanging heat between an effluent fluid and a first and a second and a third treatment fluid in a heat exchanger according to claim 8, wherein the effluent fluid is passed through a first fluid circuit and the first treatment fluid is passed through the second fluid circuit, the second treatment fluid is passed through a third fluid circuit and the third treatment fluid is passed through the fourth fluid circuit, the method comprising:

passing the effluent fluid along one side of a first membrane and simultaneously passing the first treatment fluid along another side of the first membrane, subsequently passing the effluent fluid along one side of a second membrane, and simultaneously passing the second treatment fluid along another side of the second membrane, subsequently passing the effluent fluid along one side of a third membrane, and simultaneously passing the third treatment fluid along another side of the third membrane, and exchanging heat between the effluent fluid and the first treatment fluid over the first membrane and exchanging heat between the effluent fluid and the second treatment fluid over the second membrane and exchanging heat between the effluent fluid and the third treatment fluid over the third membrane.

25. The method according to claim 22 wherein the effluent fluid flows is counter current to the at least one of the first, the second or the third treatment fluid flows.

26. The method according to claim 23 wherein the effluent fluid is arranged to pass through the heat exchanger such that the effluent fluid alternatingly heats a first and a second treatment fluid.

27. The method according to claim 24 wherein the effluent fluid is arranged to pass through the heat exchanger such that the effluent fluid alternatingly heats a first, a second and a third treatment fluid.

28. The method according to claim 22 wherein the treatment fluid is heated over the membrane and over another membrane.

29. The method according to claim 22 wherein the treatment fluid is heated over the membrane and at another membrane.

30. The method according to claim 23 wherein the secondary fluid circuit is interlaced with the primary fluid circuit such that the effluent fluid heats the first treatment fluid over a first membrane and heats the second treatment fluid over a second membrane.

31. The method according to claim 23 where the effluent fluid is divided into a first and a second flow and where the first flow is passed through the second fluid circuit and the second flow is passed through the third fluid circuit and where the first treatment fluid flow is passed through the first fluid circuit.

32. The method according to claim 24 where the effluent fluid is divided into a first flow, a second flow and a third flow and where the first flow is passed through the second fluid circuit, the second flow is passed through the third fluid circuit and the third flow is passed through the fourth fluid circuit and where the treatment fluid flow is passed through the first fluid circuit.

\* \* \* \* \*